(12) United States Patent
Virgil et al.

(10) Patent No.: US 11,623,377 B2
(45) Date of Patent: Apr. 11, 2023

(54) DIALYZER MANUFACTURING TOOL

(71) Applicant: Fresenius Medical Care Holdings, Inc., Waltham, MA (US)

(72) Inventors: Bryce Aaron Virgil, North Ogden, UT (US); Bill Ray Cower, Ogden, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 384 days.

(21) Appl. No.: 16/703,287

(22) Filed: Dec. 4, 2019

(65) Prior Publication Data
US 2021/0170652 A1 Jun. 10, 2021

(51) Int. Cl.
| | |
|---|---|
| B29C 45/40 | (2006.01) |
| A61M 1/16 | (2006.01) |
| B01D 61/24 | (2006.01) |
| B01D 67/00 | (2006.01) |
| B29C 45/17 | (2006.01) |
| B29C 45/26 | (2006.01) |
| B29C 45/72 | (2006.01) |

(Continued)

(52) U.S. Cl.
CPC ........... B29C 45/40 (2013.01); A61M 1/1621 (2014.02); B01D 61/243 (2013.01); B01D 67/00 (2013.01); B29C 45/1769 (2013.01); B29C 45/2606 (2013.01); B29C 45/7207 (2013.01); *A61M 2207/00* (2013.01); *A61M 2207/10* (2013.01); *B01D 2323/42* (2013.01); *B29C 2045/2683* (2013.01); *B29C 2045/4078* (2013.01); *B29L 2031/14* (2013.01); *B29L 2031/755* (2013.01)

(58) Field of Classification Search
CPC . B29C 45/40; B29C 45/1769; B29C 45/2606; B29C 45/7207; B29C 2045/2683; B29C 2045/4078; B29C 2045/7633; B29C 2045/4266; B29C 45/4225; A61M 1/1621; A61M 2207/00; A61M 2207/10; B01D 67/00; B01D 2323/42; B29L 2031/14; B29L 2031/755; B25J 9/023; B25J 15/0052; B25J 15/0616
See application file for complete search history.

(56) References Cited

FOREIGN PATENT DOCUMENTS

| | | |
|---|---|---|
| CN | 104260282 | 3/2017 |
| JP | H07-205219 | 8/1995 |

(Continued)

OTHER PUBLICATIONS

PCT International Search Report and Written Opinion in International Appln. No. PCT/US2020/061110, dated Mar. 10, 2021, 15 pages.

(Continued)

*Primary Examiner* — Timothy Kennedy
*Assistant Examiner* — Olukorede Esan
(74) *Attorney, Agent, or Firm* — Fish & Richardson P.C.

(57) ABSTRACT

A dialyzer housing manufacturing system includes a molding device configured to mold a dialyzer housing, and a tool coupled to a robotic arm and configured to retrieve the dialyzer housing from the molding device after the dialyzer housing is molded. The tool includes a frame, a first suction cup connected to a first portion of the frame, and a second suction cup connected to a second portion of the frame, the second suction cup being oriented about 70 degrees to about 110 degrees relative to the first suction cup.

24 Claims, 21 Drawing Sheets

(51) Int. Cl.
*B29L 31/14* (2006.01)
*B29L 31/00* (2006.01)

(56) References Cited

FOREIGN PATENT DOCUMENTS

| JP | H07205219 A | * | 8/1995 | ............ | B29C 45/42 |
|----|-------------|---|--------|--------------|------------|
| JP | 2007-245436 |   | 9/2007 |              |            |

OTHER PUBLICATIONS

International Preliminary Report on Patentability in International Appln. No. PCT/US2020/061110, dated Jun. 16, 2022, 10 pages.

* cited by examiner

DIALYZER MANUFACTURING TOOL

TECHNICAL FIELD

This disclosure relates to a robotic arm tool for use in dialyzer manufacturing.

BACKGROUND

Hemodialysis is a treatment used to support a patient with insufficient renal function. During hemodialysis, a patient's blood is passed through a dialyzer of a dialysis machine while also passing a dialysis solution or dialysate through the dialyzer. Dialyzers include a housing and a semi-permeable membrane contained within the housing of the dialyzer. The semi-permeable membrane separates the blood from the dialysate within the dialyzer and allows diffusion and osmosis exchanges to take place between the dialysate and the blood stream. The housings of dialyzers are typically manufactured using an injection molding process.

SUMMARY

In one aspect, a dialyzer housing manufacturing system includes a molding device configured to mold a dialyzer housing, and a tool coupled to a robotic arm and configured to retrieve the dialyzer housing from the molding device after the dialyzer housing is molded. The tool includes a frame, a first suction cup connected to a first portion of the frame, and a second suction cup connected to a second portion of the frame, the second suction cup being oriented about 70 degrees to about 110 degrees relative to the first suction cup.

Embodiments can include one or more of the following features in any combination.

In certain embodiments, the first and second suction cups are fluidly coupled to a vacuum source.

In some embodiments, the dialyzer housing manufacturing system further includes a third suction cup connected to the first portion of the frame, a fourth suction cup connected to the first portion of the frame, a fifth suction cup connected to the first portion of the frame, a sixth suction cup connected to the second portion of the frame, a seventh suction cup connected to the second portion of the frame; and an eighth suction cup connected to the second portion of the frame, the sixth, seventh, and eighth suction cups being oriented about 70 degrees to about 110 degrees relative to the third, fourth, and fifth suction cups.

In certain embodiments, the molding device is configured to mold two dialyzer housings.

In some embodiments, the tool is configured to simultaneously retrieve two dialyzer housings from the molding device.

In certain embodiments, the molding device is an injection molding device.

In some embodiments, the tool is rotatable between a first position and a second position.

In certain embodiments, the dialyzer housing manufacturing system further includes a pneumatic cylinder, and a rotation pin, wherein the rotation pin couples the tool to the robotic arm, and the tool is configured to rotate about the rotation pin in response to a force applied to the tool by the pneumatic cylinder.

In some embodiments, a width of the tool in the first position is about 16 cm to about 17 cm.

In certain embodiments, the molding device is configured to open a pair of mold halves between about 200 mm to about 240 mm after molding the dialyzer housing.

In some embodiments, a width of the tool in the second position is about 35 cm to about 36 cm.

In certain embodiments, the mold includes an alignment pin coupled to a first half of the mold, and the alignment pin remains partially inserted into a second half of the mold when the mold is opened after molding the dialyzer housing.

In some embodiments, the dialyzer housing manufacturing system further includes a cooling table for cooling the dialyzer housing.

In certain embodiments, the dialyzer housing manufacturing system further includes a storage container for storing the dialyzer housing.

In a further aspect, a method includes opening a mold to expose a first dialyzer housing, coupling the first dialyzer housing to a first portion of a tool, moving the tool to remove the first dialyzer housing from the mold, rotating the tool about 70 degrees to about 110 degrees to orient the first portion of the tool in a first direction, placing the first dialyzer housing at a first location using the tool, rotating the tool about 70 degrees to about 110 degrees to orient a second portion of the tool in the first direction, coupling a second dialyzer housing at the first location to the second portion of the tool, and placing the second dialyzer housing at a second location using the tool.

Embodiments can include one or more of the following features in any combination.

In some embodiments, the mold is opened about 200 mm to about 240 mm.

In certain embodiments, coupling the first dialyzer housing to a first portion of a tool includes inserting the tool between a first half of the mold and a second half of the mold.

In some embodiments, inserting the tool between a first half of the mold and the second half of the mold includes extending a robotic arm coupled to the tool between the first half of the mold and the second half of the mold.

In certain embodiments, coupling the first dialyzer housing to the first portion of the tool includes positioning one or more suction cups coupled to the first portion of the tool proximate the first dialyzer housing, and applying vacuum suction through an opening in each of the one or more suction cups.

In some embodiments, placing the first dialyzer housing at a first location using the tool includes positioning the first dialyzer housing proximate the first location using the tool, and stopping the application of vacuum suction through the opening of each of the one or more suction cups.

In certain embodiments, coupling a second dialyzer housing at the first location to the second portion of the tool includes positioning one or more suction cups coupled to the second portion of the tool proximate the second dialyzer housing, and applying vacuum suction through an opening in each of the one or more suction cups.

In some embodiments, placing the second dialyzer housing at a second location using the tool includes positioning the second dialyzer housing proximate the second location using the tool, and stopping the application of vacuum suction through the opening of each of the one or more suction cups.

In certain embodiments, the method further includes coupling a third dialyzer housing to the first portion of the tool, and moving the tool to remove the third dialyzer housing from the mold, wherein the first dialyzer housing and the third dialyzer housing are removed from the mold simultaneously.

In some embodiments, the method further includes coupling a fourth dialyzer housing at the first location to the second portion of the tool, and placing the fourth dialyzer housing at the second location using the tool, wherein the second dialyzer housing and the fourth dialyzer housing are placed at the second location simultaneously.

In certain embodiments, the first location comprises a cooling table.

In some embodiments, the second location comprises a storage container.

In a further aspect, a device for removing a dialyzer housing from a mold includes a tool coupled to a robotic arm, and a pin rotatably coupling the tool to the robotic arm. The tool includes a frame, a first suction cup connected to a first portion of the frame, and a second suction cup connected to a second portion of the frame, the second suction cup being oriented about 70 degrees to about 110 degrees relative to the first suction cup.

Embodiments can include one or more of the following features in any combination.

In certain embodiments, the first and second suction cups are fluidly coupled to a vacuum source.

In some embodiments, the device further includes a third suction cup connected to the first portion of the frame, a fourth suction cup connected to the first portion of the frame, a fifth suction cup connected to the first portion of the frame, a sixth suction cup connected to the second portion of the frame, a seventh suction cup connected to the second portion of the frame, and an eighth suction cup connected to the second portion of the frame, the sixth, seventh, and eighth suction cups being oriented about 70 degrees to about 110 degrees relative to the third, fourth, and fifth suction cups.

In certain embodiments, the tool is configured to rotate about 70 degrees to about 110 degrees between a first position and second position about the pin.

In some embodiments, a width of the tool in the first position is about 16 cm to about 17 cm.

In certain embodiments, a width of the tool in the second position is about 35 cm to about 36 cm.

In a further aspect, a dialyzer housing manufacturing system includes a molding device configured to mold a dialyzer housing, and a tool coupled to a robotic arm and configured to retrieve the dialyzer housing from the molding device after the dialyzer housing is molded. The tool includes a frame, a first suction cup connected to a first portion of the frame, and a second suction cup connected to a second portion of the frame, wherein the tool is rotatable between a first position in which the first suction cup extends in a first direction and a second position in which the second suction cup extends in the first direction, and the width of the tool in the second position is greater than the width of the tool in the first position.

The width of the tool in the first position is measured linearly from the first suction cup to an opposite edge of the tool, and the width of the tool in the second position is measured linearly from the second suction cup to an opposite edge of the tool.

Advantages of the systems, devices, and methods described herein include reduced wear on the injection molding device. For example, by using a rotatable arm tool to minimize the amount that the mold must be opened during removal of a dialyzer housing from the mold ("de-molding"), the amount of wear on the injection molding device is reduced. In addition, by using a rotatable arm tool to minimize the amount that the mold must be opened during de-molding, the alignment pins of the molding device can remain engaged during de-molding, which reduces the risk of damage to the injection molding device. Another advantage is that the overall time required to perform injection molding of the dialyzer housing is reduced by using a rotatable arm tool to minimize the amount the mold must be opened during de-molding.

Other aspects, features, and advantages will be apparent from the description and drawings, and from the claims

DETAILED DESCRIPTION

Figure 1:
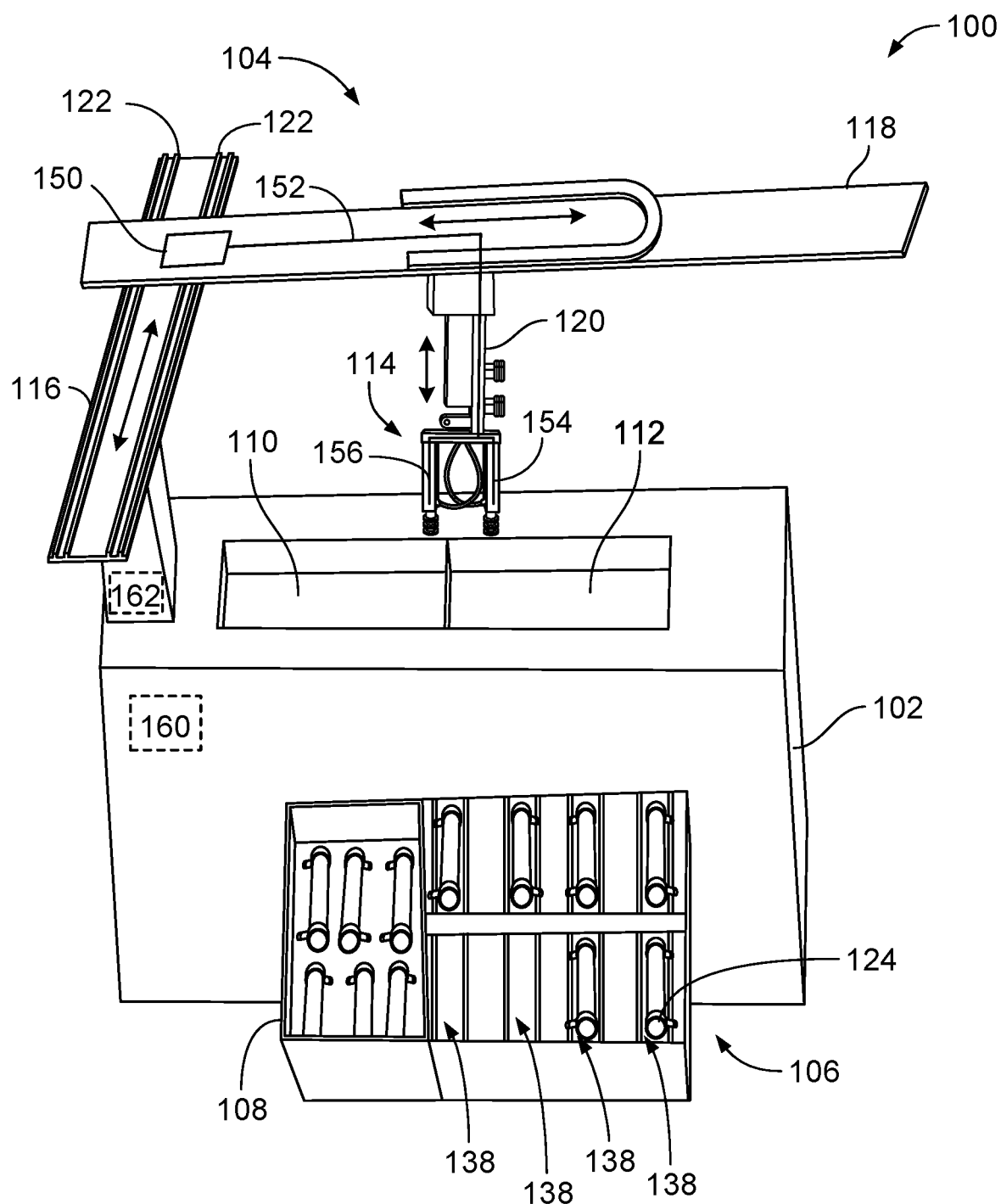
FIG. 1 depicts a system for manufacturing a dialyzer housing that includes a molding device and a robotic arm tool.

Referring to FIG. 1, a dialyzer housing manufacturing system 100 includes an injection molding device 102, a robotic arm 104, a cooling table 106, and a storage container 108.

As depicted in FIG. 1, the injection mold includes two mold halves 110, 112. As described in further detail herein, the mold halves 110, 112 can move within the injection molding device 102 to form a cavity in which a dialyzer housing 124 can be molded. For example, as depicted in FIG. 1, during injection molding of the dialyzer housing 124, the mold halves 110, 112 are pressed together and molten resin is injected into the cavity formed by the mold halves 110, 112 to mold the dialyzer housing 124. Once the dialyzer housing 124 is molded, the mold halves 110, 112 open to expose the dialyzer housing 124 and allow for retrieval of the dialyzer housing 124 from the injection molding device 102.

Once the dialyzer housing has been formed by the injection molding device 102, the robotic arm 104 is used to retrieve the dialyzer housing 124 from the injection molding device 102. As depicted in FIG. 1, an arm tool 114 is coupled to an end of the robotic arm 104. As described in further detail herein, the arm tool 114 can apply a suction force to the dialyzer housings 124 to remove the dialyzer housings 124 from the injection molding device 102.

Once the dialyzer housing 124 has been removed from the injection molding device 102 using the arm tool 114, the robotic arm 104 and arm tool 114 are used to place the dialyzer housing 124 on the cooling table 106. For example, the arm tool 114 can rotate about the end of the robotic arm 104 to position a dialyzer housing 124 coupled to the arm tool 114 on the cooling table 106. The cooling table 106 is configured to provide air flow around the dialyzer housing 124 to reduce the temperature of the surface of the newly molded dialyzer housing 124. As depicted in FIG. 1, the cooling table 106 includes multiple cooling racks 138, which allows for multiple dialyzer housings 124 to be positioned on the cooling table 106.

Once the surface of the dialyzer housing 124 has cooled to a temperature ranging from about 115° C. to about 125° C., a portion of the arm tool 114 couples to the dialyzer housing 124. The robotic arm 104 and the arm tool 114 lifts the dialyzer housing 124 off the cooling table 106 and places the dialyzer housing 124 within the storage container 108. Once the storage container 108 is filled with dialyzer housings, a new, empty storage container is provided, and the filled storage container 108 can be used to store or ship the dialyzer housings packed within the storage container 108.

Still referring to FIG. 1, the robotic arm 104 of the dialyzer housing manufacturing system 100 includes a base 116, a lateral boom 118, and a vertical projection 120. The base 116 is stationary relative to the injection molding device 102 and includes a set of tracks 122 extending along the length of a top surface of the base 116. The position of the arm tool 114 can be adjusted by moving various components of the robotic arm 104. For example, the vertical projection 120 can traverse along the length on the lateral boom 118 and the lateral boom can traverse crosswise along the length of the base 116 by traveling along the tracks 122. In addition, the vertical projection 120 is configured to extend to lower the arm tool 114 and retract to raise the arm tool 114. By coordinating the movements of the lateral boom 118 and the vertical projection 120, the arm tool 114 can be precisely positioned within three dimensional space.

As depicted in FIG. 1, the dialyzer housing manufacturing system 100 also includes a set of controllers 160, 162. A first controller 160 is configured to control the injection molding device 102, and a second controller 162 is configured to control the robotic arm 104 and the arm tool 114. The controllers 160, 162 are communicatively coupled with each other and send signal to one another to coordinate the movements of the injection molding device 102, the robotic arm 104, and the arm tool 114. By controlling the timing and movements of the injection molding device 102, the robotic arm 104, and the arm tool 114, the controllers 160, 162 enable the arm tool 114 to engage and move dialyzer housings 124 throughout the dialyzer housing manufacturing system 100. For example, the injection molding device controller 160 signals the robotic arm controller 162 when the molds 110, 112 are in an open position and the robotic arm controller 162 controls the robotic arm 104 and arm tool 114 to retrieve the dialyzer housings from the molds 110, 112.

Further, the injection molding device 102 and the robotic arm 104 each include rotary encoder(s) (not shown) that are communicably coupled to the controllers 160, 162, and signals received by the controllers 160, 162 from the rotary encoder(s) can be used to determine the spatial positioning of the components of the injection molding device 102 and robotic arm 104. For example, rotary encoder(s) are used to measure the number of rotations of the motor(s) of the robotic arm 104 has completed. The controller 162 can determine the direction and distance that the lateral boom 118 and/or vertical projection 120 of the robotic arm 104 has travelled based on the number of rotations that the motor(s) of the robotic arm 104 has completed, as detected by the rotary encoder(s). Based on determining the direction and distance that the lateral boom 118 and/or vertical projection 120 has travelled based on the signals received from the rotary encoder(s), the controller 162 can determine the position of the arm tool 114 in three-dimensional space. Similarly, rotary encoders are used to measure the number of rotations of the motor(s) used to move the mold 110, 112 has completed. The controller 160 can determine the direction and distance that the mold half 112 of the injection molding device 102 has travelled based on the number of rotations that the motor(s) of the injection molding device 102 has completed, as detected by the rotary encoder(s). Each of the components of the injection molding device 102 and the robotic arm 104 are configured to move predetermined distances throughout the process cycle in order to conduct molding and transporting the dialyzer housings. In some embodiments, the rotary encoders of the injection molding device 102 and the robotic arm 104 each determine the number of rotations that the motor(s) of the injection molding device 102 and the robotic arm 104, respectively, have completed based on signals received from a proximity switch(es) communicably coupled to the encoders. In some embodiments, the rotary encoders of the injection molding device 102 and the robotic arm 104 each determine the number of rotations that the motor(s) of the injection molding device 102 and the robotic arm 104, respectively, have completed based on magnets of the rotary encoders.

Figure 2:
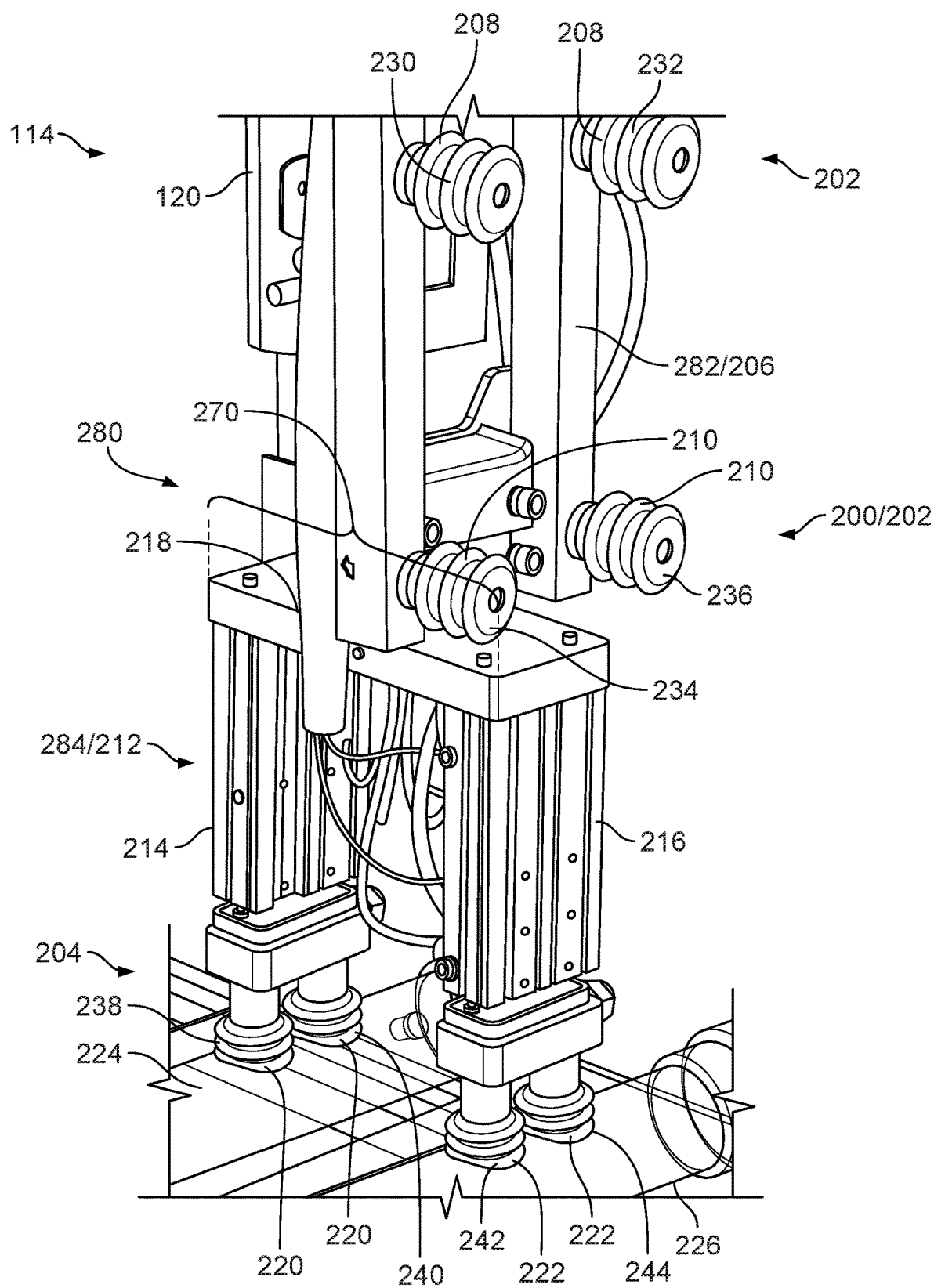
FIG. 2 is a perspective view of the robotic arm tool of the system of FIG. 1 in a first position.

FIG. 2 depicts a perspective view of the arm tool 114 in a first position 200. As depicted in FIG. 2, the arm tool 114 includes eight suction cups 230, 232, 234, 236, 238, 240, 242, 244 coupled to a frame 280.

Each suction cup 230, 232, 234, 236, 238, 240, 242, 244 is configured to couple to a dialyzer housing 124 that is formed by the injection molding device 102. For example, each suction cup 230, 232, 234, 236, 238, 240, 242, 244 includes an opening through its center, and each suction cup 230, 232, 234, 236, 238, 240, 242, 244 is fluidly coupled to a vacuum source, enabling suction to be applied through the center of each suction cup 230, 232, 234, 236, 238, 240, 242, 244. As described in further detail herein, a dialyzer housing can be coupled to the suction cups 230, 232, 234, 236, 238, 240, 242, 244 by applying suction through the center of the respective suction cup.

Figure 3:
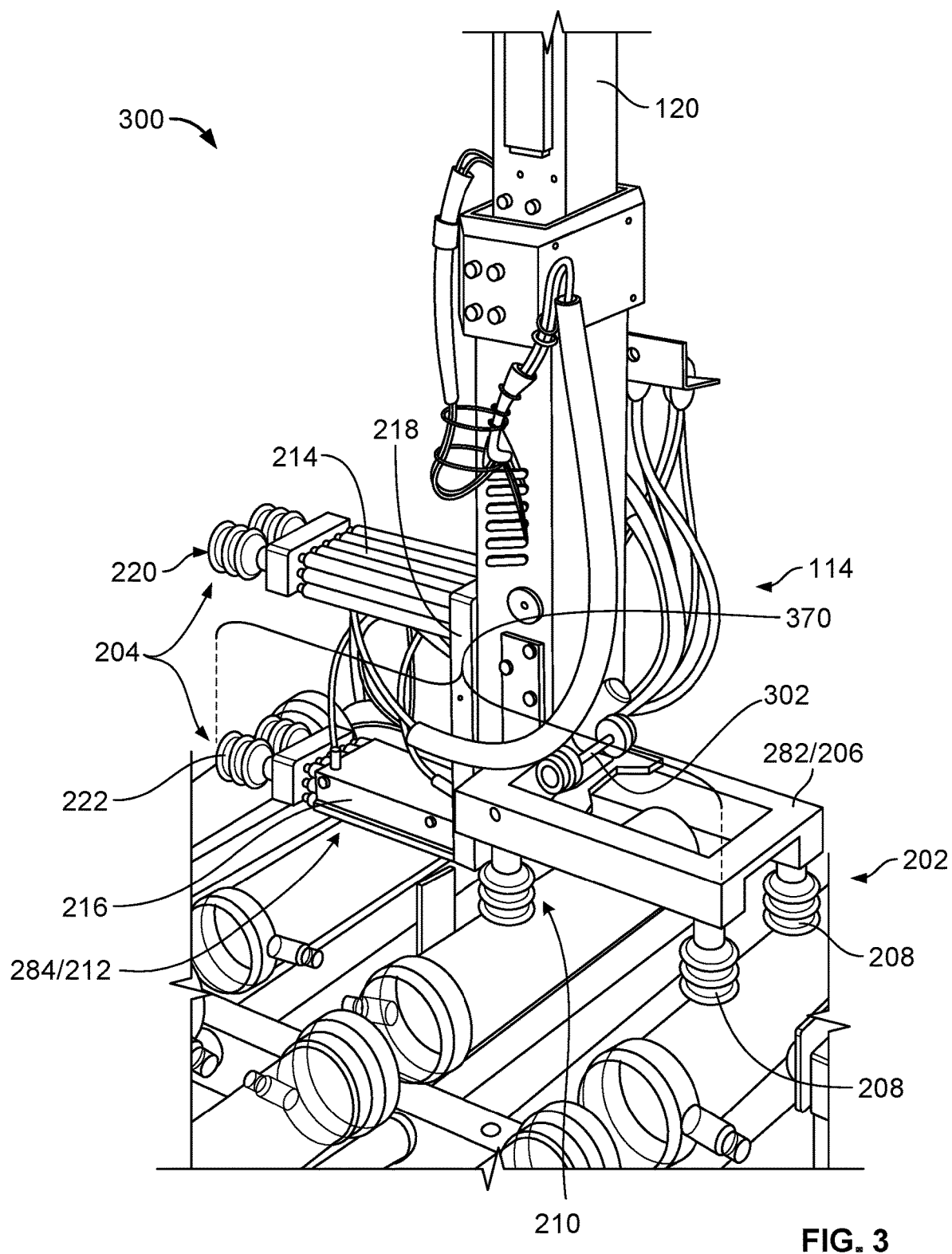
FIG. 3 is a perspective view of the robotic arm tool of the system of FIG. 1 in a second position.

The suction cups 230, 232, 234, 236, 238, 240, 242, 244 are divided into a first set of suction cups 202, which includes suction cups 230, 232, 234, 236, and a second set of suction cups 204, which includes suction cups 238, 240, 242, 244. As depicted in FIG. 2, the first set of suction cups 202 is coupled to a first portion 282 of the frame 280, and the second set of suction cups 204 is coupled to a second portion 284 of the frame 280. As can be seen in FIGS. 2 and 3, the first set of suction cups 202 are coupled to the frame 280 such that the first set 202 is oriented about 90 degrees relative to the second set of suction cups 204.

Referring to FIG. 1, the system 100 includes a vacuum source 150 that is fluidly coupled to each set of suction cups 202, 204 via a vacuum line 152 that extends along the vertical projection 120. The controller 160 controls the application of vacuum suction through each set of suction cups 202, 204 to allow for selective engagement of dialyzer housings to the sets of suction cups 202, 204. The vacuum source 150 applies a vacuum pressure in a range of about 0.35 MPa to about 0.50 MPa to the ends of each of the suction cups. Any of various suitable pumps can be used as the vacuum source 150, such as a suction pump, a positive displacement pump, a venturi pump, etc.

The vacuum source 150 is communicatively coupled to a controller 160, which controls the timing of the application of suction by the vacuum source 150 through the sets 202, 204 of suction cups of the arm tool 114. For example, the controller 160 can coordinate the vacuum suction with the movements of the robotic arm 104 and the arm tool 114 in order to selectively apply vacuum suction through one of the sets of suction cups 202, 204 when the respective set is positioned proximate a dialyzer housing to be moved by the arm tool 114.

As depicted in FIG. 2, the first portion 282 of the frame 280 forms a rectangular platform 206 and the first set of suction cups 202 is attached to the rectangular platform 206. When the arm tool 114 is in a first position 200 (as depicted in FIG. 1), the rectangular platform 206 is positioned such that the first set of suction cups 202 coupled to the platform 206 point sideways relative to the vertical projection 120 of the robotic arm 104. As depicted in FIG. 2, the first set of suction cups 202 includes two pairs of suction cups 208, 210. Each suction cup 230, 232, 234, 236 in the first set 202 is coupled to the rectangular platform 206 proximate a respective corner of the rectangular platform 206.

The first set of suctions cups 202 is configured to simultaneously couple to two dialyzer housings, with the first pair of suction cups 208 coupling to a first dialyzer housing and the second pair of suction cups 210 coupling to a second dialyzer housing. As previously discussed, each of the suction cups in the first set 202 includes an opening therethrough. The first set of suction cups 202 are fluidly coupled to the vacuum line 152, which is coupled to the vacuum source 150, and vacuum suction can be provided through the vacuum line 152 to the first set of suction cups 202 in order to couple a pair of dialyzer housings to the first set of suction cups 202.

In some examples, the rectangular platform 206 has a total width of about 9 cm to about 11 cm (e.g., about 10.16 cm), a total length of about 16 cm to about 17 cm (e.g., about 16.51 cm), and a total thickness of about 1 cm to about 3 cm (e.g., about 2.54 cm).

Still referring to FIG. 2, the second portion 284 of the frame 280 forms a U-shaped platform 212, and the second set of suction cups 204 is attached to a U-shaped platform 212. The U-shaped platform 212 includes a first post 214, a second post 216, and a connector bar 218. The first post 214 is coupled to a first end of the connector bar 218 and the second post 216 is coupled to a second end of the connector bar 218 opposite the first post 214. As depicted in FIG. 2, the longitudinal axis of the connector bar 218 is substantially perpendicular to the longitudinal axis of each of the posts 214, 216. When the arm tool 114 is in the first position 200 (as depicted in FIG. 2), the longitudinal axis of each of the posts 214, 216 is substantially parallel to the longitudinal axis of the vertical projection 120 of the robotic arm 104. As depicted in FIG. 2, the rectangular platform 206 is coupled to the connector bar 218 of the U-shaped platform 212.

In some examples, each post 214, 216 of the U-shaped platform 212 has a total width of about 7 cm to about 8 cm (e.g., about 7.62 cm), a total length of about 22 cm to about 24 cm (e.g., about 25.4 cm), and a total thickness of about 1 cm to about 3 cm (e.g., about 3.81 cm). In some examples, the connector bar 218 of the U-shaped platform 212 has a total width of about 7 cm to about 8 cm (e.g., about 7.62 cm), a total length of about 16 cm to about 17 cm (e.g., about 16.51 cm), and a total thickness of about 1 cm to about 3 cm (e.g., about 2.54 cm).

Similar to the first set of suction cups 202, the second set of suction cups 204 also includes a first pair of suction cups 220 and a second pair of suction cups 222, totaling four suction cups in the second set 204. As depicted in FIG. 2, the first pair of suction cups 220 of the second set 204 is coupled to an end of the first post 214, and the second pair of suction cups 222 of the second set 204 is coupled to an end of the second post 216.

As depicted in FIG. 2, the second set of suctions cups 204 is configured to couple to two dialyzer housings, with the first pair of suction cups 220 coupling to a first dialyzer housing 224 and the second pair of suction cups 222 coupling to a second dialyzer housing 226. For example, as previously discussed, each of the suction cups in the second set 204 includes an opening therethrough. In addition, the posts 214, 216 each include a vacuum line 154, 156, respectively, coupled to vacuum line 152 to allow suction to be applied through second set of suction cups 204 to couple a pair of dialyzer housings to the second set of suction cups 204.

FIG. 3 depicts the arm tool 114 in a second position 300. As shown in FIG. 3, when the arm tool 114 is in the second position 300, the longitudinal axis of each of the posts 214, 216 of the U-shaped platform 212 are perpendicular to the longitudinal axis of the vertical projection 120 of the robotic arm 104. In addition, when the arm tool 114 is in the second position 300, the first set of suction cups 202 coupled to the rectangular platform 206 are facing downward.

As depicted in FIG. 3, the arm tool 114 is coupled to an end of the vertical projection 120 of the robotic arm 104 using a pin connector 302, and is rotatable about the end the vertical projection 120 via the pin connector 302. For example, the arm tool 114 can rotate about 0 degrees to about 90 degrees about the pin connector 302. In some embodiments, the arm tool 114 rotates about 90 degrees about the pin connector 302 between the first position 200 (depicted in FIG. 2) and the second position 300 (depicted in FIG. 3). The arm tool 114 also includes a pneumatic cylinder (not shown), which applies a force to an end of the arm tool 114 and causes the arm tool to rotate about the pin connector 302. The controller 160 controls and coordinates the rotation of the arm tool 114 between the first position 200 and the second position 300 during manufacturing and packaging the dialyzer housings. For example, the controller 160 signals the pneumatic cylinder of the arm tool 114 to extend or retract to rotate the arm tool 114 between the first position 200 and the second position 300.

As can be seen in FIGS. 2 and 3, the width 270 of the profile of the arm tool 114 in the first position 200 is smaller than the width 370 of the profile of the arm tool 114 in the second position 300. For example the width 270 of the profile of the arm tool 114 in the first position 200 can be about 16 cm to about 17 cm (e.g., about 16.5 cm), and the width 370 of the profile of the arm tool 114 in the second position 300 can be about 35 cm to about 36 cm (e.g., about 35.5 cm). The width 270 of the profile of the arm tool 114 in the first position 200 can be about 18 cm to about 20 cm less than the width 370 of the profile of the arm tool 114 in the second position 300. As depicted in FIG. 2, the width 270 of the tool 114 in the first position 200 is measured linearly from the first set of suction cups 202 to an opposite edge of the tool. As depicted in FIG. 3, the width 370 of the tool 114 in the second position 300 is measured linearly from the second set of suction cups 204 to an opposite edge of the tool 114.

Rotating the arm tool 114 between the first position 200 and the second position 300 reduces the amount the injection molding device 102 must be opened to enable the arm tool 114 to fit between the molds 110, 112, while still allowing the arm tool 114 to reach the bottom of the storage container 108 to place the dialyzer housings within the storage container 108. Minimizing the amount the injection molding device 102 must be opened to enable the arm tool 114 to remove the dialyzer housing 124 from the mold halves 110, 112 can reduce the wear on the molds 110, 112. In addition, minimizing the amount the mold halves 110, 112 must be opened during de-molding can reduce the risk of misalignment of the mold halves 110, 112, and can thus reduce the risk of damage to the injection molding device 102. Further, minimizing the amount the injection molding device 102 must be opened during de-molding can reduce the time required to open the molding injection device 102 during de-molding, which can reduce the overall time required to manufacture the dialyzer housing 124.

Figure 4:
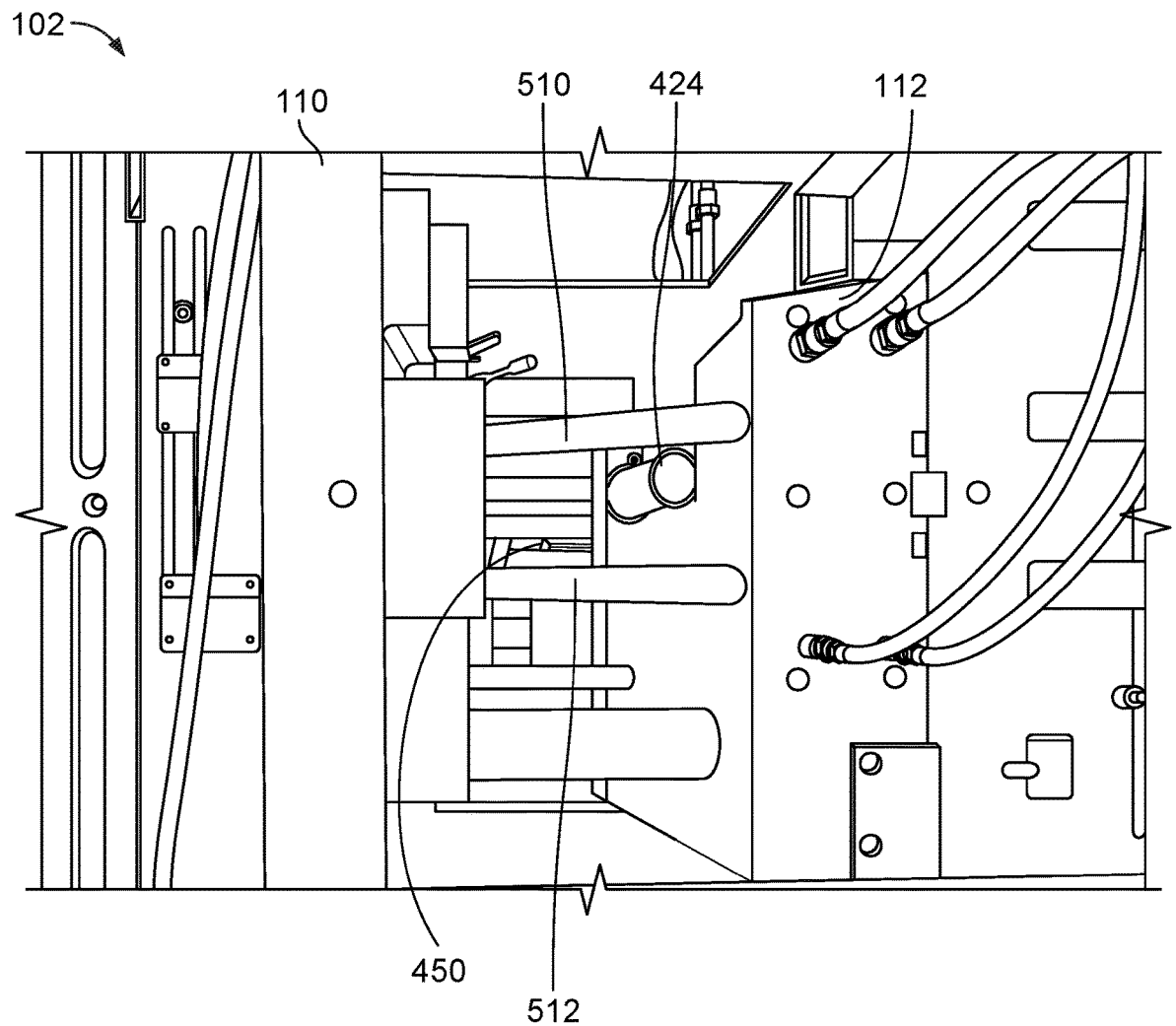
FIG. 4 is a side view of the molding device of the system of FIG. 1.

FIG. 4 depicts a side view of the injection molding device 102 of the dialyzer housing manufacturing system 100. As depicted in FIG. 4, the injection molding device 102 includes a first mold half 110 and a second mold half 112. The mold halves 110, 112 of the injection molding device 102 are configured to form two dialyzer housings at the same time.

Figure 5:
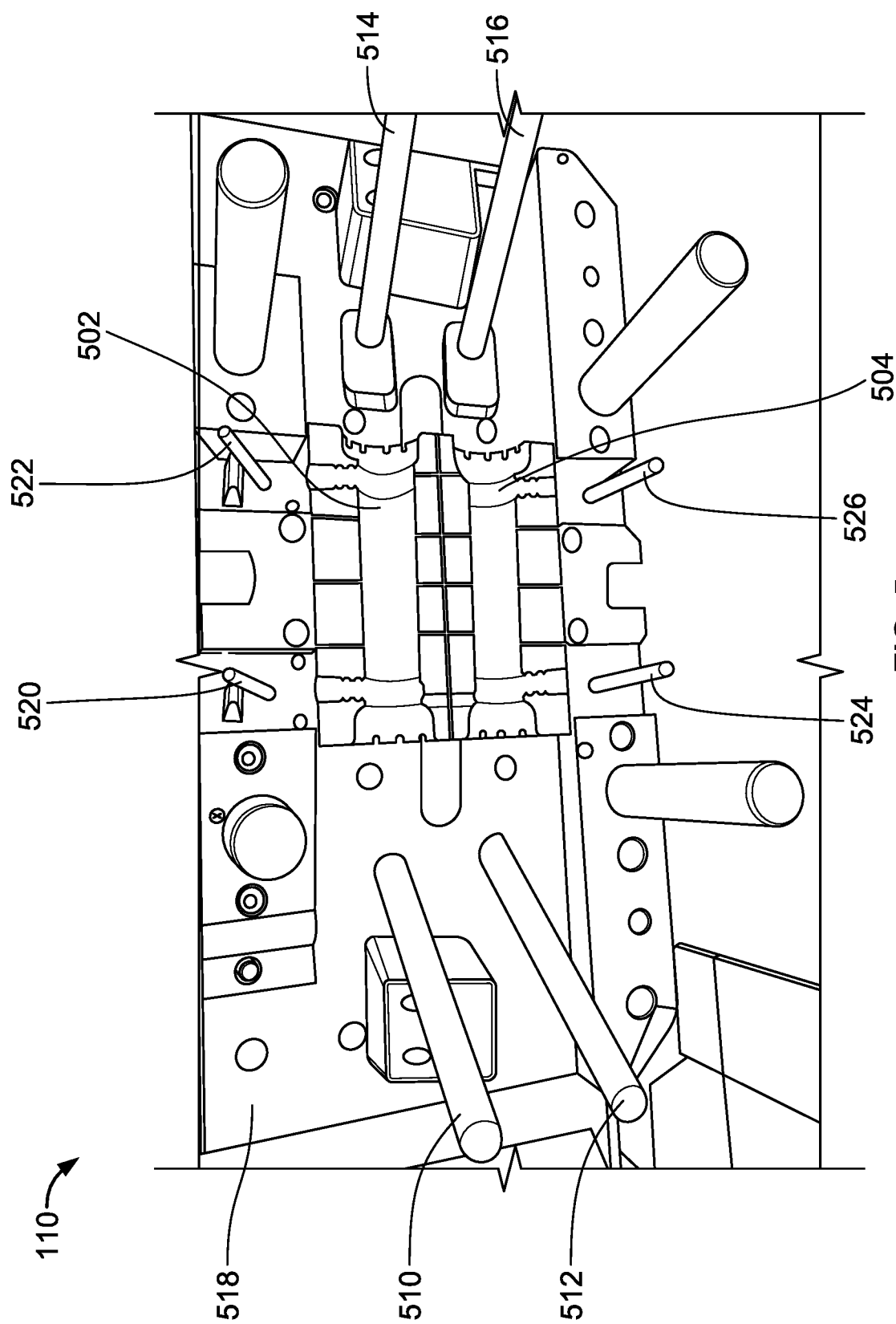
FIG. 5 is a front view of a portion of the molding device of the system of FIG. 1.

FIG. 5 depicts a front view of the first mold half 110 of the injection molding device 102. As depicted in FIG. 5, the first mold half 110 includes two cavities 502, 504 and multiple alignment pins 510, 512, 514, 516, 520, 522, 524, 526.

The cavities 502, 504 are each used to form a dialyzer housing 124. The second mold half 112 includes two corresponding cavities (not shown). During injection molding, the cavities 502, 504 of the first mold half 110 and the cavities of the second mold half 112 are aligned, the mold halves 110, 112 are positioned against one another, and molten material is injected into the cavities. As the injected material cools, the material takes the form of the cavities in the first and second mold halves 110, 112 to form the dialyzer housings 124. The dialyzer housings 124 can be formed of any of various different medical grade materials. Examples of such materials include polycarbonate, polypropylene, etc.

As depicted in FIG. 5, the first mold half 110 includes a first set of four mold alignment pins 510, 512, 514, 516 and a second set of mold alignment pins 520, 522, 524, 526 projecting outward from the interior surface 518 of the first mold half 110. The mold alignment pins 510, 512, 514, 516, 520, 522, 524, 526 ensure proper alignment and a secure fitting between the two mold halves 110, 112 during injection molding. For example, when the mold halves 110, 112 of the injection molding device 102 are properly aligned, the mold alignment pins 510, 512, 514, 516, 520, 522, 524, 526 align with and are inserted into corresponding openings in the second mold half 112 (not shown).

As depicted in FIG. 4, once the injection molding is complete, the second mold half 112 is moved apart from first mold half 110 by a predetermined distance 450 to expose the dialyzer housings formed by the injection molding device 102. In some cases, the second mold half 112 is moved about 230 mm apart from the first mold half 110 to accommodate the insertion of the arm tool 114 (positioned in the first position 200) between the mold halves 110, 112. The arm tool 114 is used to remove the dialyzer housings 424 from the second mold half 112.

As depicted in FIG. 4, the mold alignment pins 510, 512, 514, 516 and core alignment pins 520, 522, 524, 526 of the second mold half 112 remain at least partially inserted in the corresponding openings in the first mold half 110 throughout the injection molding process. By positioning the arm tool 114 in the first position 200 to minimize the distance between the mold halves 110, 112 required to insert arm tool 114 between the mold halves 110, 112, the alignment pins 510, 512, 514, 516, 520, 522, 524, 526 of the second mold half 112 can remain partially inserted in the openings of the first mold half 110 during de-molding. Leaving the alignment pins 510, 512, 514, 516, 520, 522, 524, 526 of the second mold half 112 partially inserted in the first mold half 110 during de-molding reduces the risk of misalignment of the mold halves 110, 112 and reduces the risk of damage to the mold halves 110, 112.

The second mold half 112 also includes ejector pins (not shown) that are used to eject the formed dialyzer housings 424 from the second mold half 112. As described in further detail herein, the controller 160 coordinates the movement of the ejector pins and the application of suction through the vacuum line 152 to the arm tool 114 such that the ejector pins eject the dialyzer housings 424 from the mold 112 and the arm tool 114 provides suction and couples to the dialyzer housings 424 simultaneously.

A method of manufacturing and packing dialyzer housings will now be described with references to FIGS. 6-21.

Figure 6:
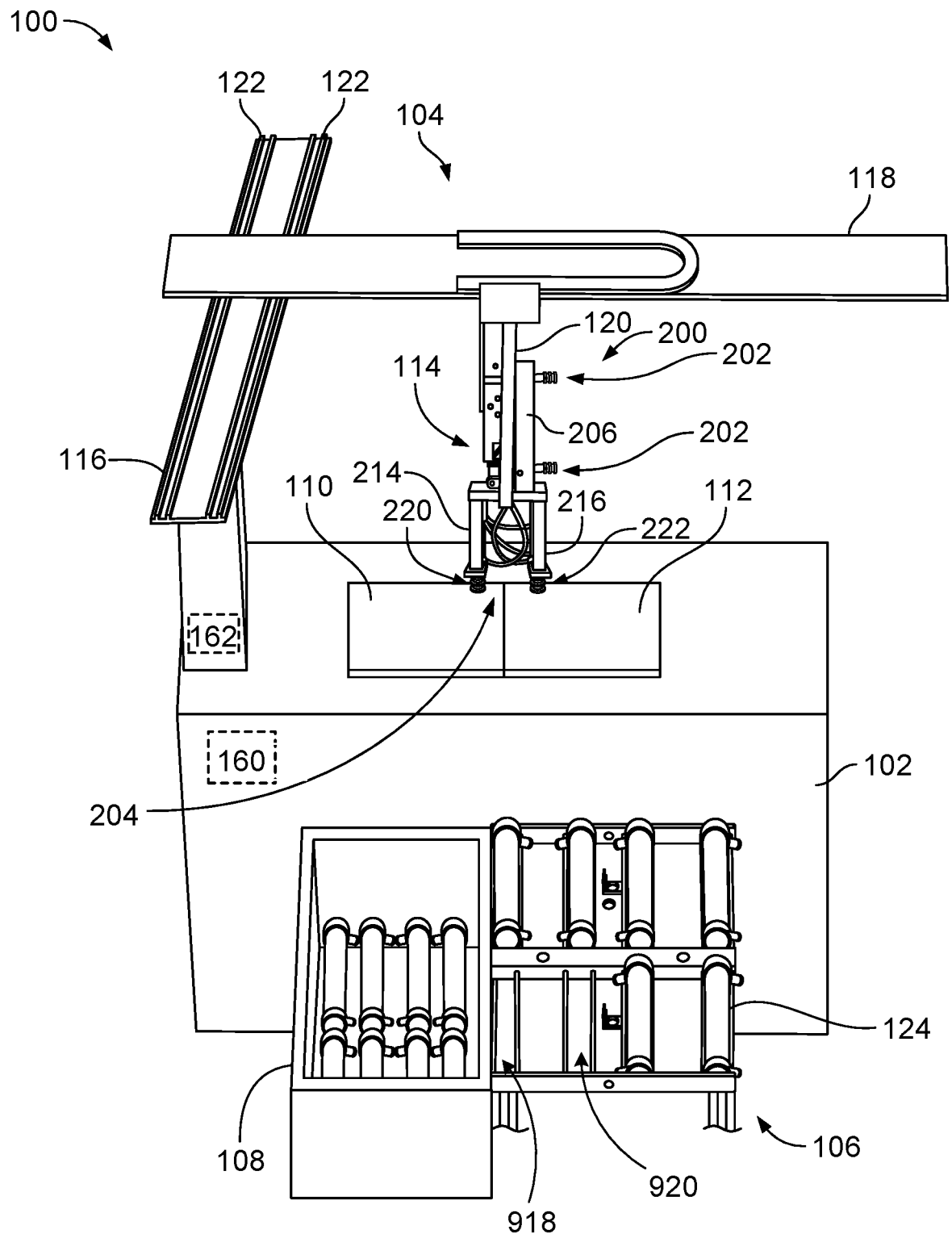
FIGS. 6-21 depict an example process for manufacturing a dialyzer housing using the system of FIG. 1.

As depicted in FIG. 6, the mold halves 110, 112 are closed while the injection molding device 102 performs injection molding of a pair of dialyzer housings (not shown). While the injection molding device 102 performs injection molding of the dialyzer housings, the robotic arm 104 is in a retracted position such that the arm tool 114 is positioned over the mold halves 110, 112. As depicted in FIG. 6, the arm tool 114 is in the first position 200 such that the posts 214, 216 of the U-shaped platform and the second set of suction cups 204 are pointing downward, and the first set of suction cups 202 are oriented laterally relative to the vertical projection 120.

Figure 7:
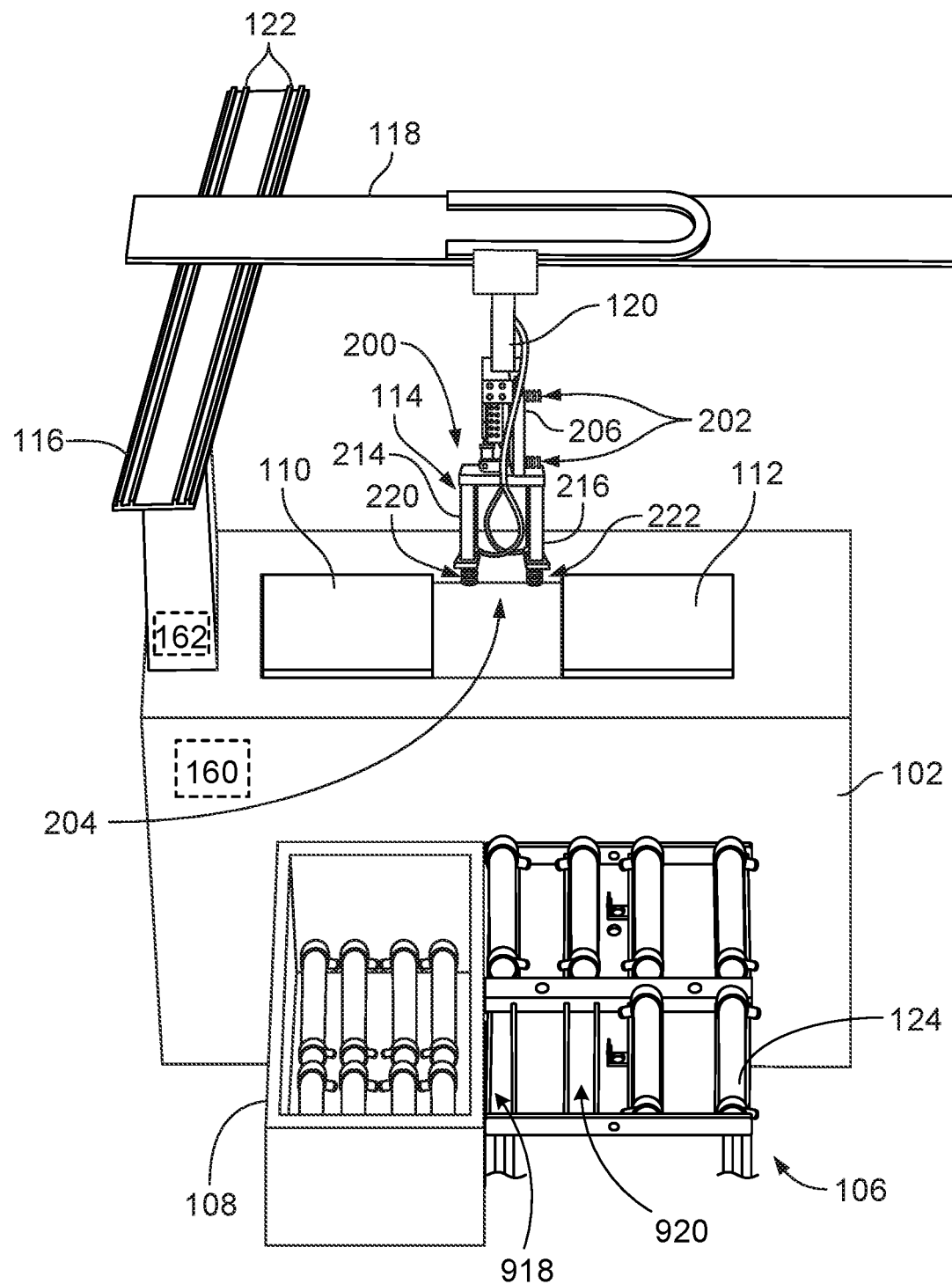

Referring to FIG. 7, once injection molding of the dialyzer housings by the injection molding device 102 is complete, the second mold half 112 retracts and moves apart from the first mold half 110 to expose the dialyzer housings. The distance between the mold halves 110, 112 is sized to allow the arm tool 114 in the first position 200 to be inserted between the mold halves 110, 112 with the first set of suction cups 202 facing the second mold half 112. For example, the distance between the mold halves 110, 112 in the open position following injection molding is between about 230 mm to accommodate the insertion of the arm tool 114 positioned in the first position 200 between the mold halves 110, 112. As previously discussed, the alignment pins 510, 512, 514, 516, 520, 522, 524, 526 of the second mold half 112 remain partially inserted in the openings of the first mold half 110 through the entire manufacturing process. The controller 160 controls the movement of the second mold half 112 to move apart from the first mold half 110 by a predetermined distance to open the mold.

Figure 8:
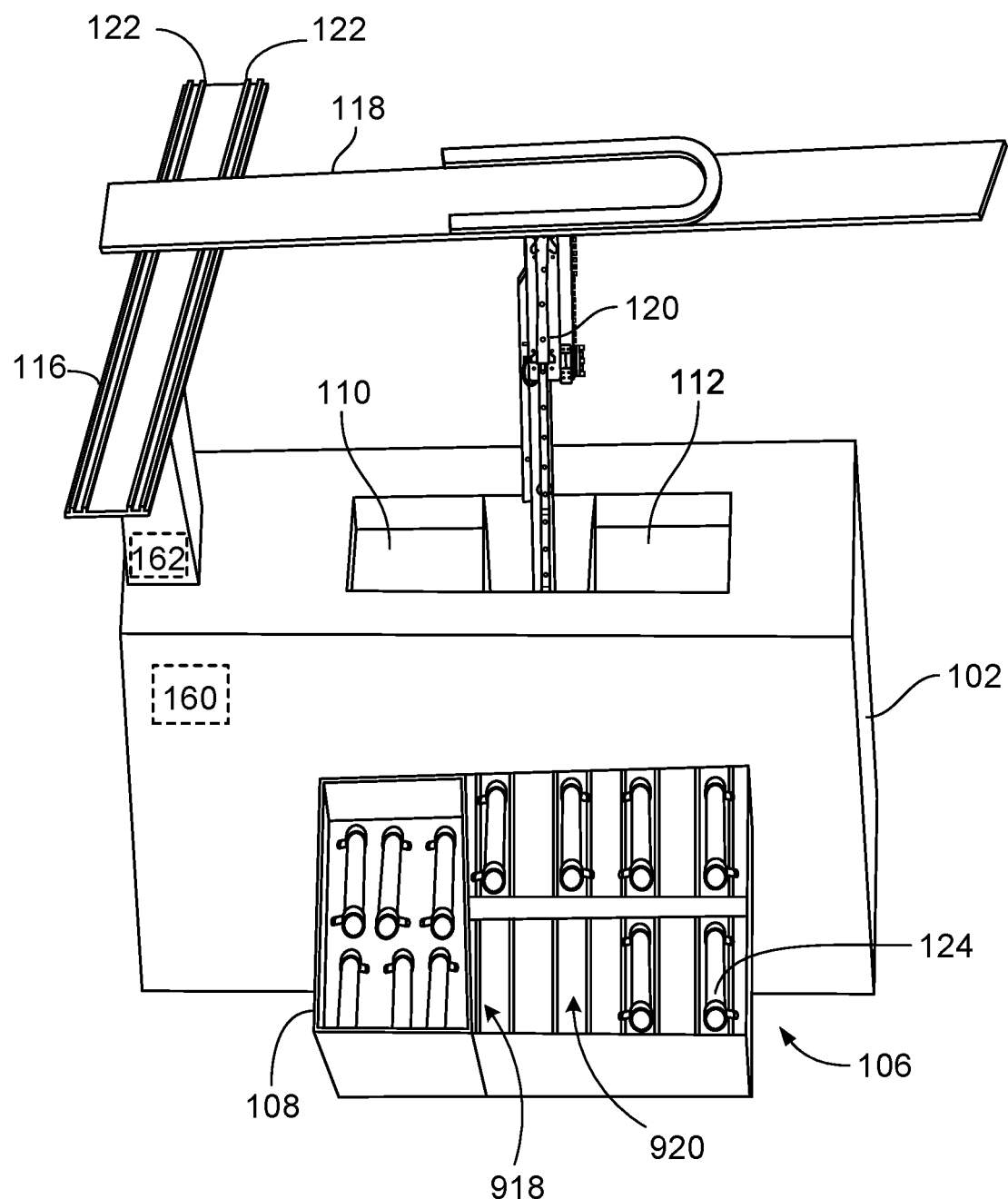

As depicted in FIG. 8, once the injection molding process is complete and the controller determines, based on signals received from rotary encoders (not shown) in the injection molding device 102, that the second mold half 112 has moved a predetermined amount (e.g., about 230 mm) to expose the dialyzer housings, the controller 160 for the injection molding device 102 transmits a signal to the controller 162 for the robotic arm 104 to indicate that the mold 110, 112 is open. In response to receiving a signal from the controller 160 of the injection molding device 102 indicating that the mold 110, 112 is open, the controller 162 of the robotic arm 104 controls the vertical projection 120 of the robotic arm 104 to extend to insert the arm tool 114 between the first mold half 110 and the second mold half 112. The vertical projection 120 of the robotic arm 104 continues to extend until the controller 162 for the robotic arm 104 determines, based on feedback received from rotary encoders (not shown) of the robotic arm 104, that the vertical projection 120 has extended a predetermined distance that corresponds to the first pair of suction cups 208 of the first set 202 being vertically aligned with a first dialyzer housing in the second mold half 112 and the second pair of suction cups 210 of the first set 202 being vertically aligned with a second dialyzer housing in the second mold half 112.

Figure 9:
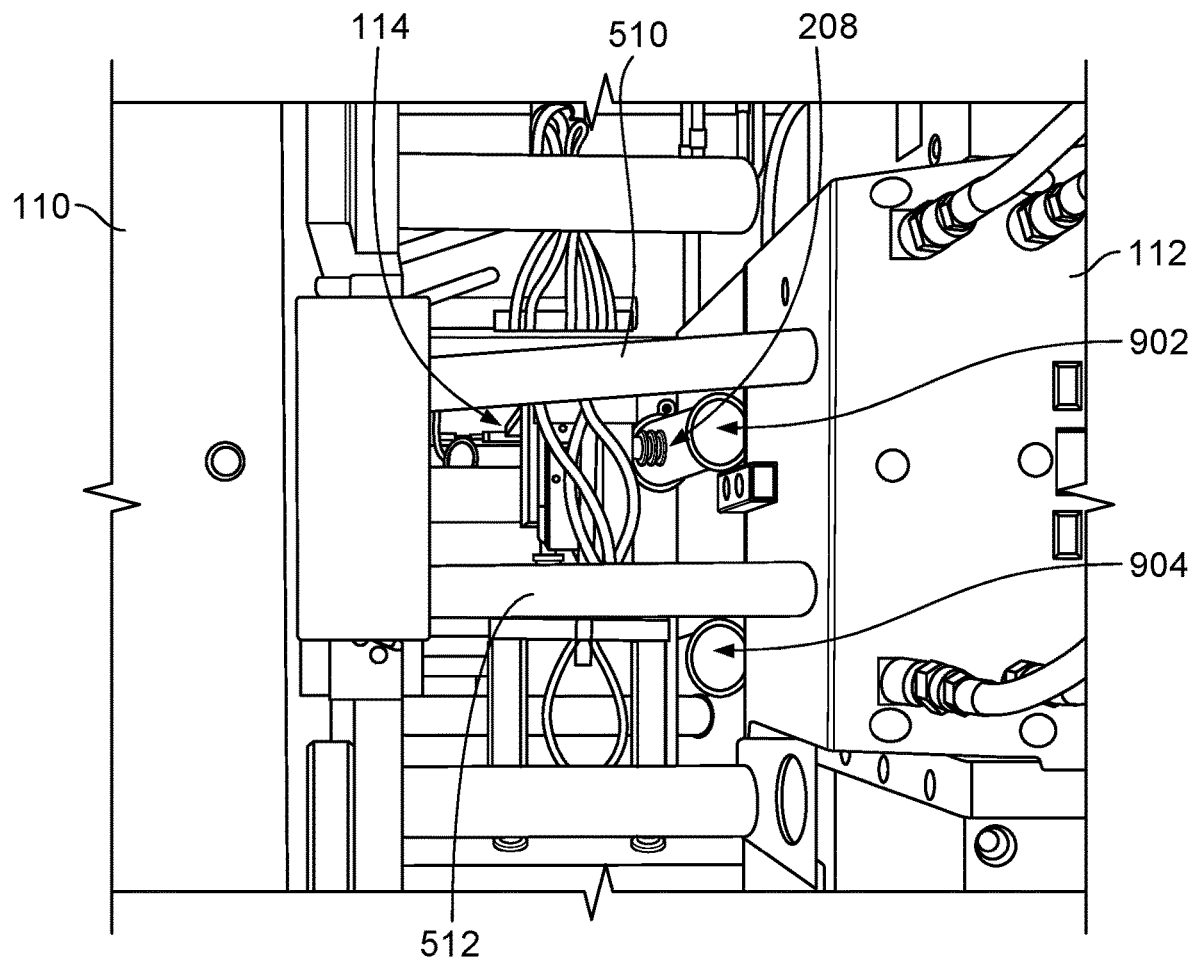

FIG. 9 depicts a side view of the molding device 102 with the arm tool 114 inserted between the mold halves 110, 112 of the molding device 102. As can be seen in FIG. 9, the first pair of suction cups 208 of the first set 202 is vertically aligned with a first dialyzer housing 902 in the second mold half 112. In addition, the second pair of suction cups 210 (not shown) of the first set 202 is vertically aligned with a second dialyzer housing 904 in the second mold half 112. As previously discussed, the controller 162 can determine the position of the arm tool 114 in three-dimensional space based on signals received from rotary encoders (not shown) of the robotic arm 104. Once the controller has reached the fixed spatial location corresponding to alignment between the pairs of suction cups 208, 210 and dialyzer housings 902, 904, the controller 162 ceases extension of the vertical projection 120.

Once the pairs of suction cups 208, 210 are vertically aligned with the dialyzer housings 902, 904, the vertical projection 120 travels along the lateral boom 118 of the robotic arm 104 until each of the suction cups in the pairs 208, 210 are moved into contact with the surface of the dialyzer housings 902, 904. For example, once the first set of suction cups 202 are vertically aligned with the dialyzer housings 902, 904, as determine by the controller 162 based on rotary encoder signals, the controller 162 controls the vertical projection 120 of the robotic arm 104 to travel laterally along the lateral boom 118 towards the second mold half 112. The vertical projection 120 continues to move towards the second mold half 112 until the controller 162 determines, based on signals received from the rotary encoder(s) of the robotic arm 104, that the coordinates of the arm tool 114 correspond to a predetermined position corresponding to the first and second pairs of suction cups 208, 210 being in contact with the surface of the dialyzer housings 902, 904, respectively.

Once the pairs of suction cups 208, 210 are each aligned with and positioned proximate the dialyzer housings 902, 904, the controller 162 initiates the application of suction through the pairs of suction cups 208, 210 and sends a signal to the controller 160 of the injection molding device 102 to move the ejector pins (not shown) of the second mold half 112. The extension of the ejector pins outwards from the second mold half 112 forces the dialyzer housings 902, 904 out of the corresponding cavities in the second mold half 112. As the ejector pins of the second mold half 112 force the dialyzer housings 902, 904 out of the mold half 112, vacuum suction is applied through each of the pairs of suction cups 208, 210 to couple the dialyzer housings 902, 904 to the first and second pairs of suction cups 208, 210, respectively. As previously discussed, each suction cup in the pairs 208, 210 includes an opening through its center, and each suction cup in the pairs 208, 210 is fluidly coupled to a vacuum source (e.g., vacuum source 150 of FIG. 1) via vacuum lines 152, 154, 156, enabling suction to be applied through the center of each suction cup. The suction applied through the pairs of suction cups 208, 210 is transferred to the surface of the dialyzer housings 902, 904, coupling the housings 902, 904 to the pairs of suction cups 208, 210 in the first set 202.

Figure 10:
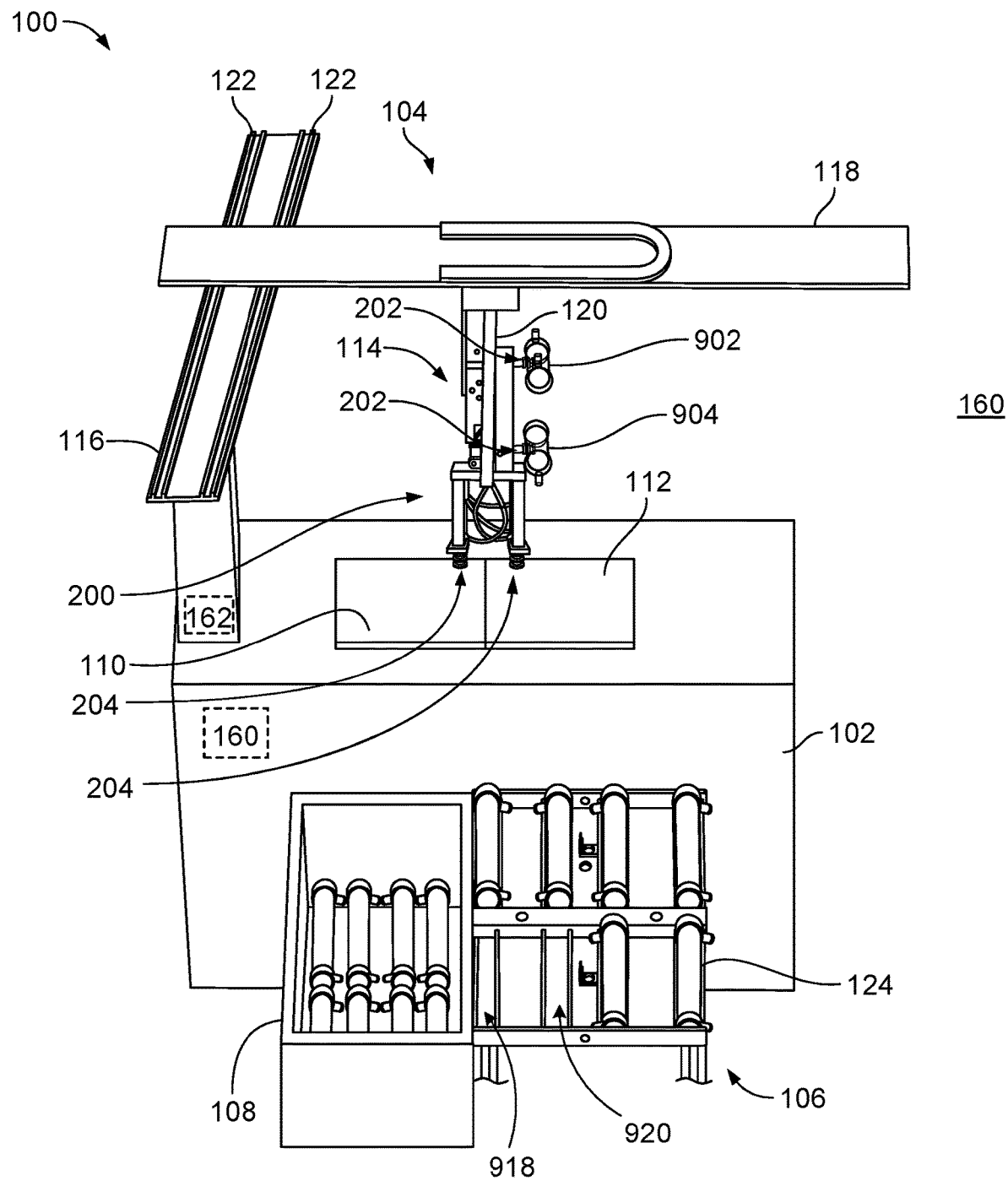

Referring to FIG. 10, once each of the dialyzer housings 902, 904 are removed from the second mold half 112 and coupled to the first set of suction cups 202 via vacuum suction, the vertical projection 120 of the robotic arm 104 is retracted and suction is continually supplied through the first set of suction cups 202 to lift the dialyzer housings 902, 904 out of the injection molding device 102. In some examples, the controller 160 determines that the dialyzer housings 902, 904 are coupled to the first set of suction cups 202 based on a signal received from a vacuum confirmation sensor (not shown) on the arm tool 114. Once the vertical projection 120 has retraced to a predetermined position to lift the dialyzer housings 902, 904 out of the injection molding device 102, the controller 162 of the robotic arm 104 sends a signal to the controller 160 of injection molding device 102. In response to receiving the signal from controller 162, the controller 160 of the injection molding device 102 controls the second mold half 112 to move the second mold half 112 towards the first mold half 110 a predetermined distance corresponding to the halves 110, 112 touching and the mold being closed, as depicted in FIG. 10. In addition, as the vertical projection 120 retracts, suction is continually applied through the first set of suction cups 202 to maintain the coupling of the dialyzer housings 902, 904 to the arm tool 114.

After lifting the dialyzer housings 902, 904 out of the injection molding device 102, the robotic arm 104 and arm tool 114 are used to place the dialyzer housings 902, 904 on a cooling table 106. FIGS. 11-15 depict a process of placing the dialyzer housings 902, 904 on the cooling table 106 using the arm tool 114.

Figure 11:
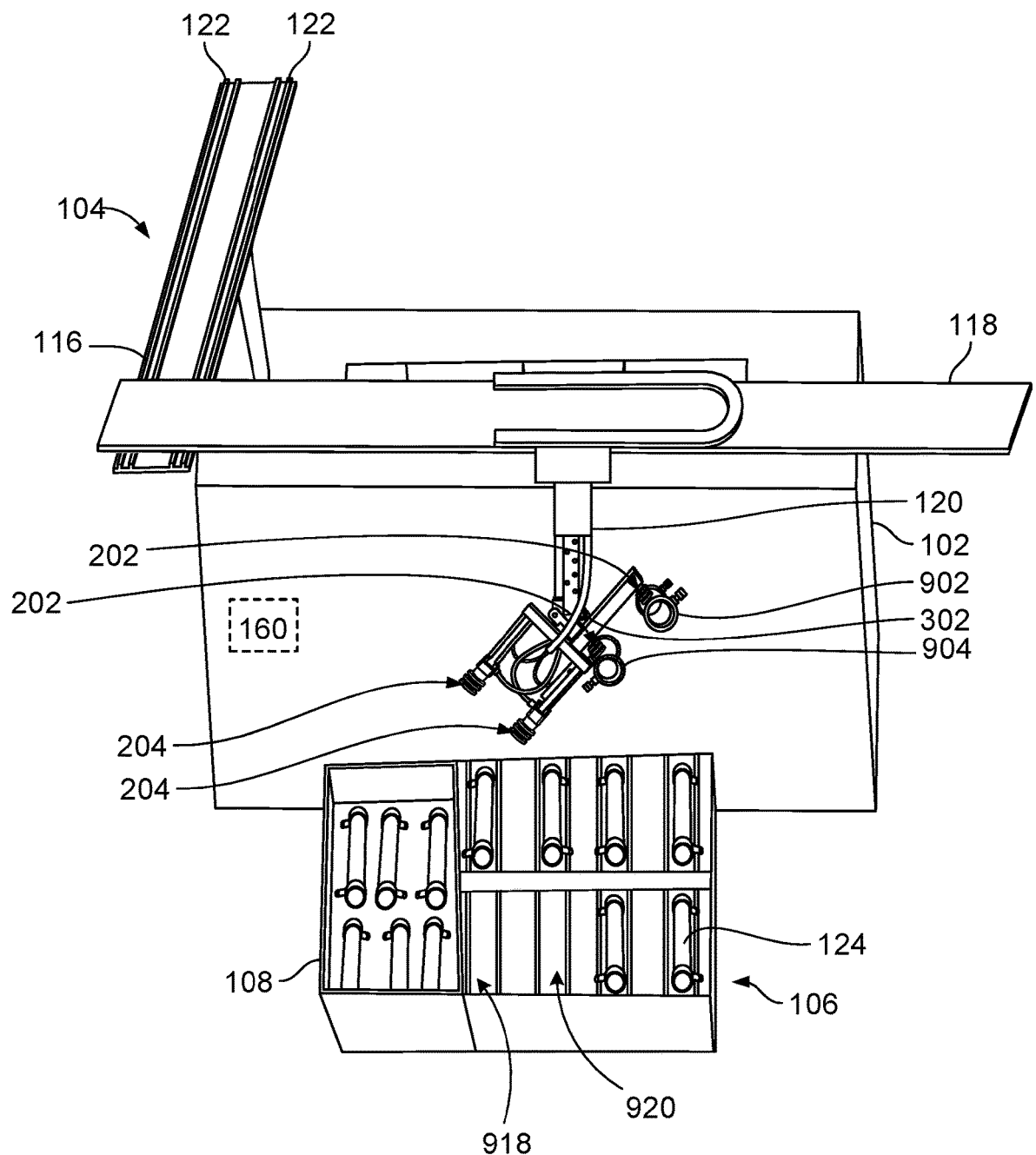

Referring to FIG. 11, with the dialyzer housings 902, 904 coupled to the first set of suction cups 202 of the arm tool 114 via vacuum suction, the lateral boom 118 of the robotic arm 104 travels forward a predetermined distance along the base 116 of the robotic arm 104. As previously discussed, the base 116 includes a set of tracks 122 along its length to allow for smooth movement of the lateral boom 118 forward and backward along the base 116. The lateral boom 118 continues to travel forward along the base 116 until the controller 160 receives a signal from the rotary encoders of the robotic arm 104 indicating that the lateral boom 118 has travelled a predetermined distance corresponding to the arm tool 114 being positioned such that the first set of suction cups 202 are positioned over a pair of empty cooling racks 918, 920 on the cooling table 106.

Still referring to FIG. 11, in addition to the lateral boom 118 travelling along the base 116, the vertical projection 120 travels laterally along the lateral boom 118 a predetermined distance to position the arm tool 114 such that the first set of suction cups 202 are positioned over a pair of empty cooling racks 918, 920 on the cooling table 106. For example, the vertical projection 120 continues to travel laterally along the lateral boom 118 until the controller 160 receives a signal from rotary encoders of the robotic arm 104 indicating that the vertical projection 120 has travelled a predetermined distance corresponding to the arm tool 114 being positioned such that the first set of suction cups 202 are positioned over a pair of empty cooling racks 918, 920 on the cooling table 106.

Figure 12:
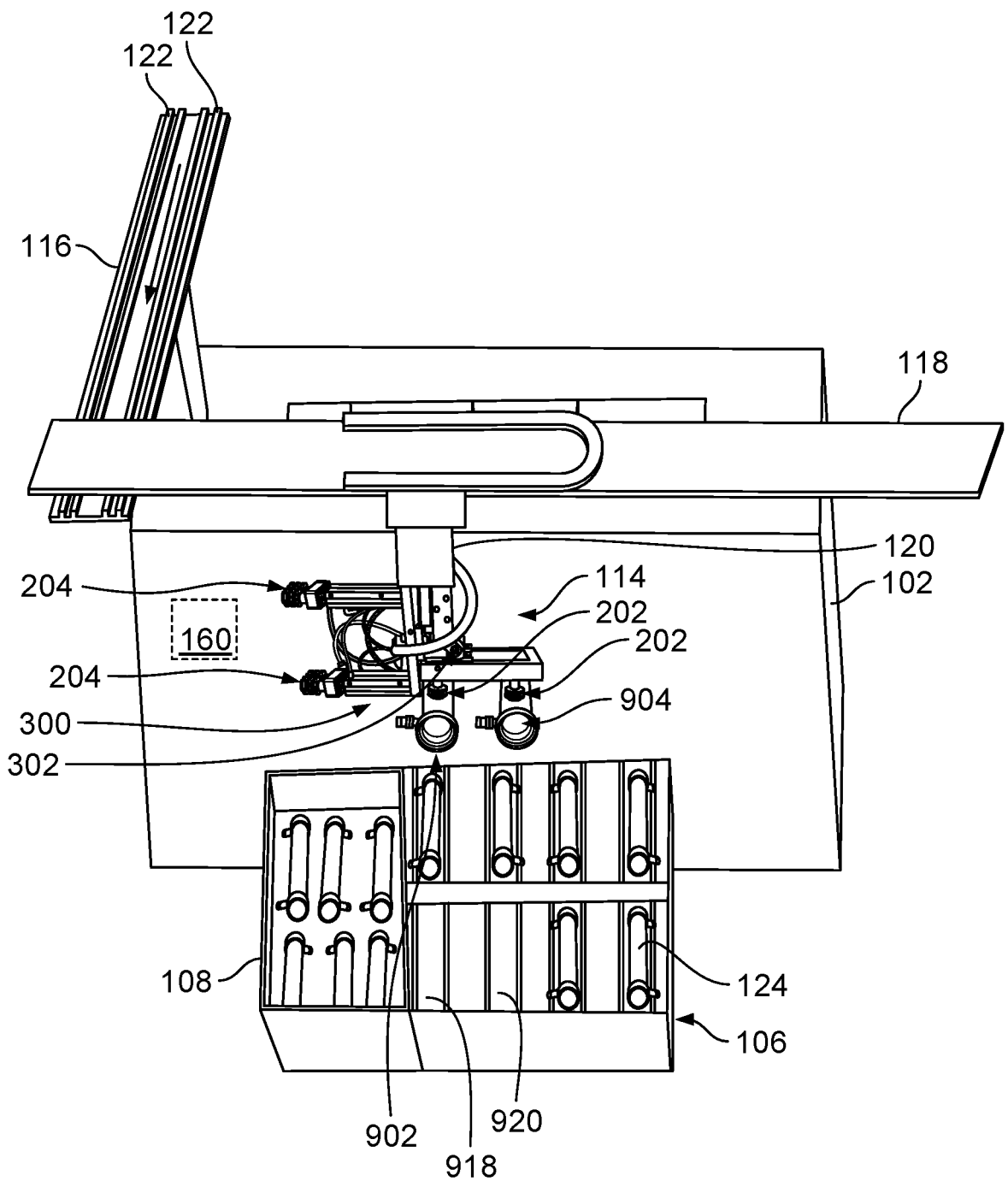

As the robotic arm 104 moves to position the arm tool 114 over the cooling racks 918, 920, the arm tool 114 rotates about the pin connector 302 to rotate the arm tool 114 from the first position 200 (as depicted in FIG. 10) to the second position 300 (as depicted in FIG. 12). FIG. 11 depicts the rotation of the arm tool between the first position 200 and the second position 300 as the robotic arm 104 travels towards the cooling table 106. As previously discussed, the arm tool 114 includes a pneumatic cylinder (not shown) that applies a force to an end of the arm tool 114 and causes the arm tool to rotate about the pin connector 302. The controller 160 coordinates the rotation of the arm tool 114 between the first fixed position 200 and the second fixed position 300 based on the current location of the arm tool 114 in three-dimensional space, as determined based on the signals received from the rotary encoders of the arm tool 114. For example, the controller 162 is programmed to rotate the arm tool 114 from the first position 200 to the second position 300 at a specific point in the sequence of movements of the manufacturing cycle and based on the position of the arm tool 114 in three-dimensional space.

FIG. 12 depicts the arm tool 114 positioned in the second position 300 with the dialyzer housings 902, 904 coupled to the first set of suction cups 202, and the first set of suction cups 202 facing downwards and aligned over the empty cooling racks 918, 920 on the cooling table 106.

Figure 13:
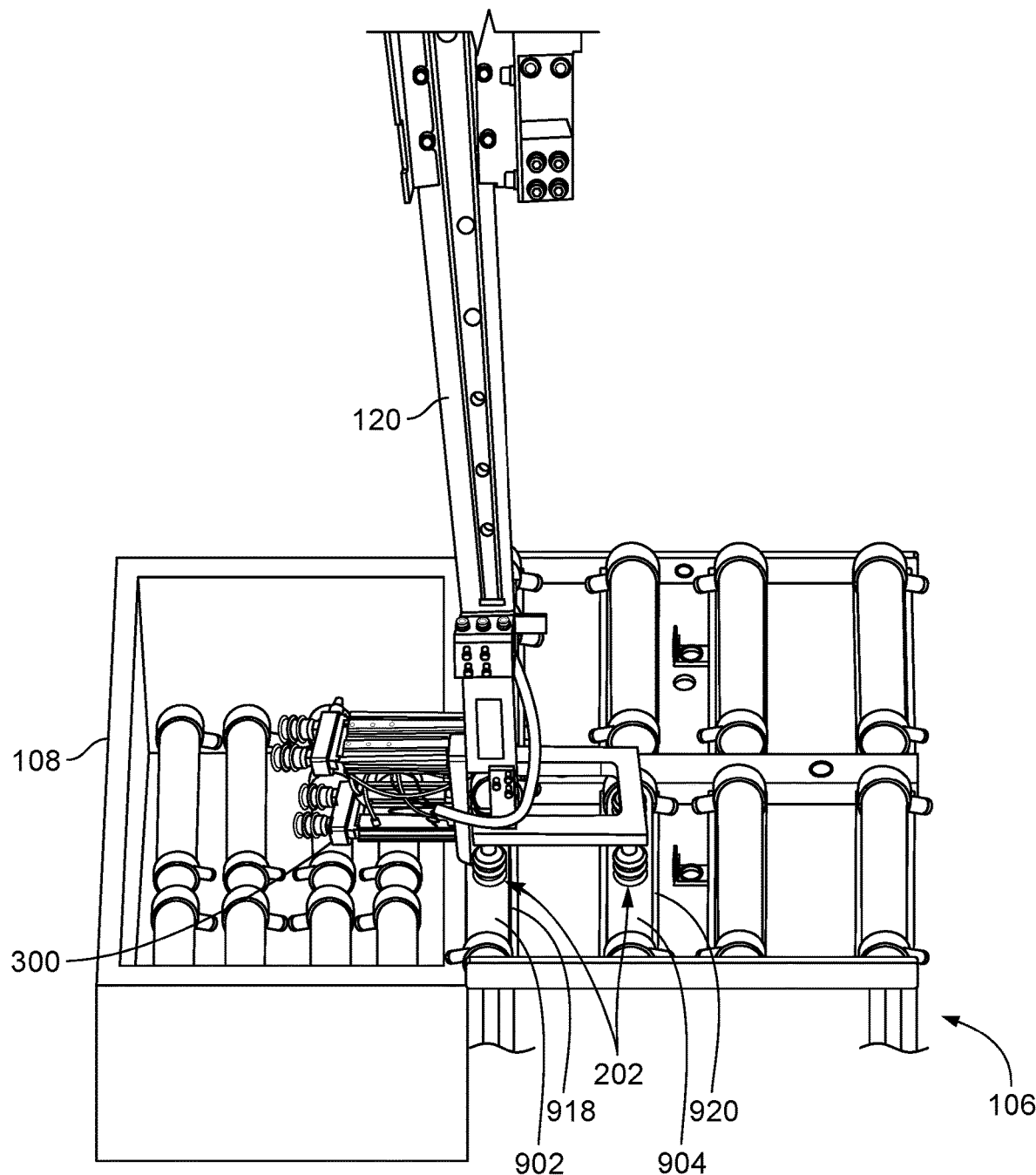
Figure 14:
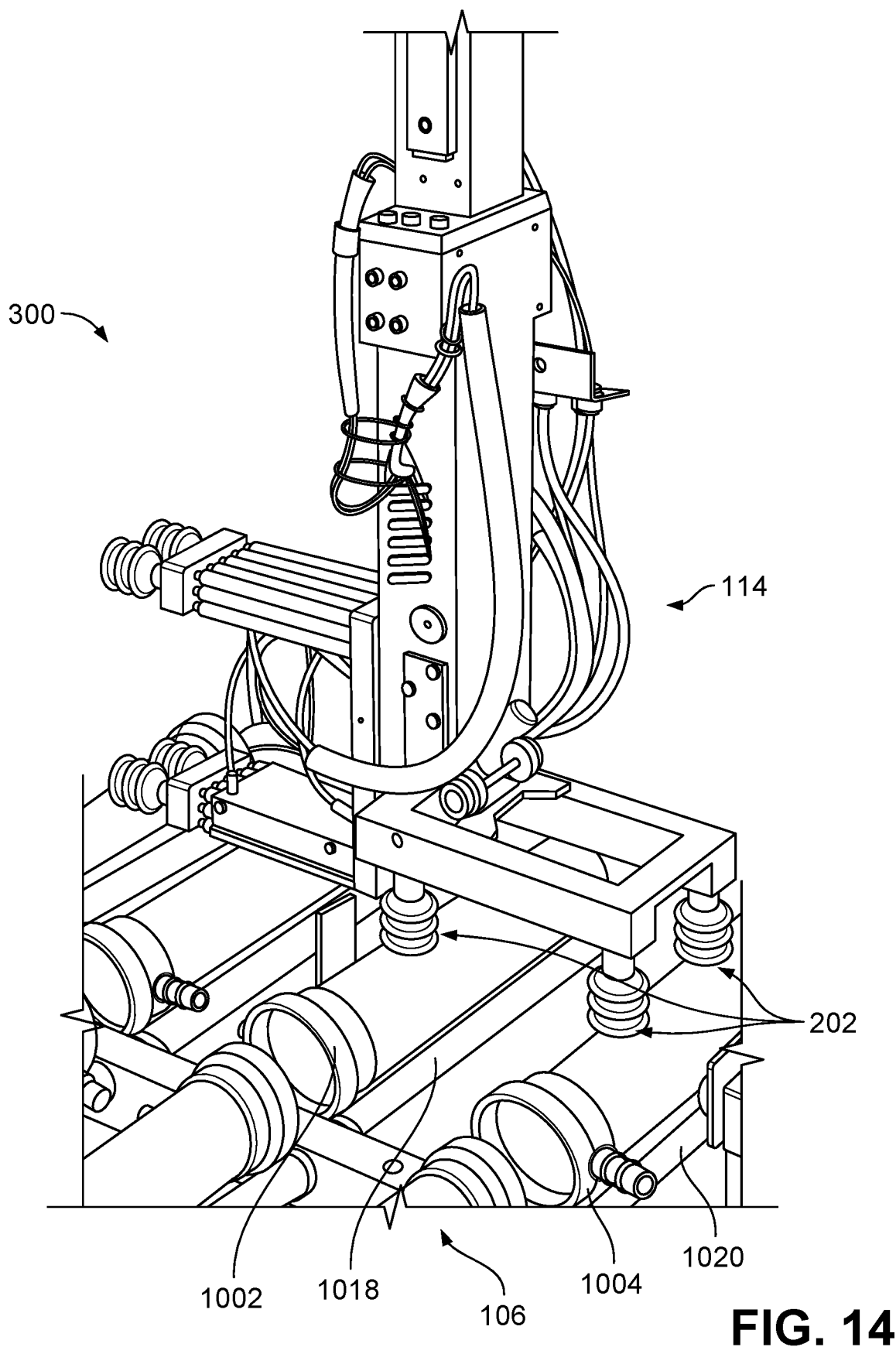

Referring to FIG. 13, once the arm tool 114 is in the second position 300 with the dialyzer housings 902, 904 aligned over the empty cooling racks 918, 920, as determined based on signals received by the controller 162 from the rotary encoder(s) of the robotic arm 104, the vertical projection 120 of the robotic arm 104 extends a predetermined amount (as detected by the rotary encoder(s) of the robotic arm) to lower the dialyzer housings 902, 904 into the respective cooling racks 918, 920. Once the robotic arm 104 has lowered the dialyzer housings 902, 904 a predetermined amount into the cooling racks 918, 920, the vacuum suction provided through the first set of suction cups 202 is stopped, which decouples the dialyzer housings 902, 904 from the arm tool 114 and releases the housings 902, 904 onto the cooling racks 918, 920. FIG. 14 depicts a perspective view of the arm tool 114 in the second position 300 releasing a pair of dialyzer housing 1002, 1004 into a pair of cooling racks 1018, 1020 on a cooling table 106.

Once the dialyzer housings 902, 904 have been placed on the cooling table 106 and released from the arm tool 114, the arm tool 114 is used to move another pair of dialyzer housings into the storage container 108. FIGS. 15-21 depict a process of moving a pair of dialyzer housings from the cooling table 106 to the storage container 108.

Figure 15:
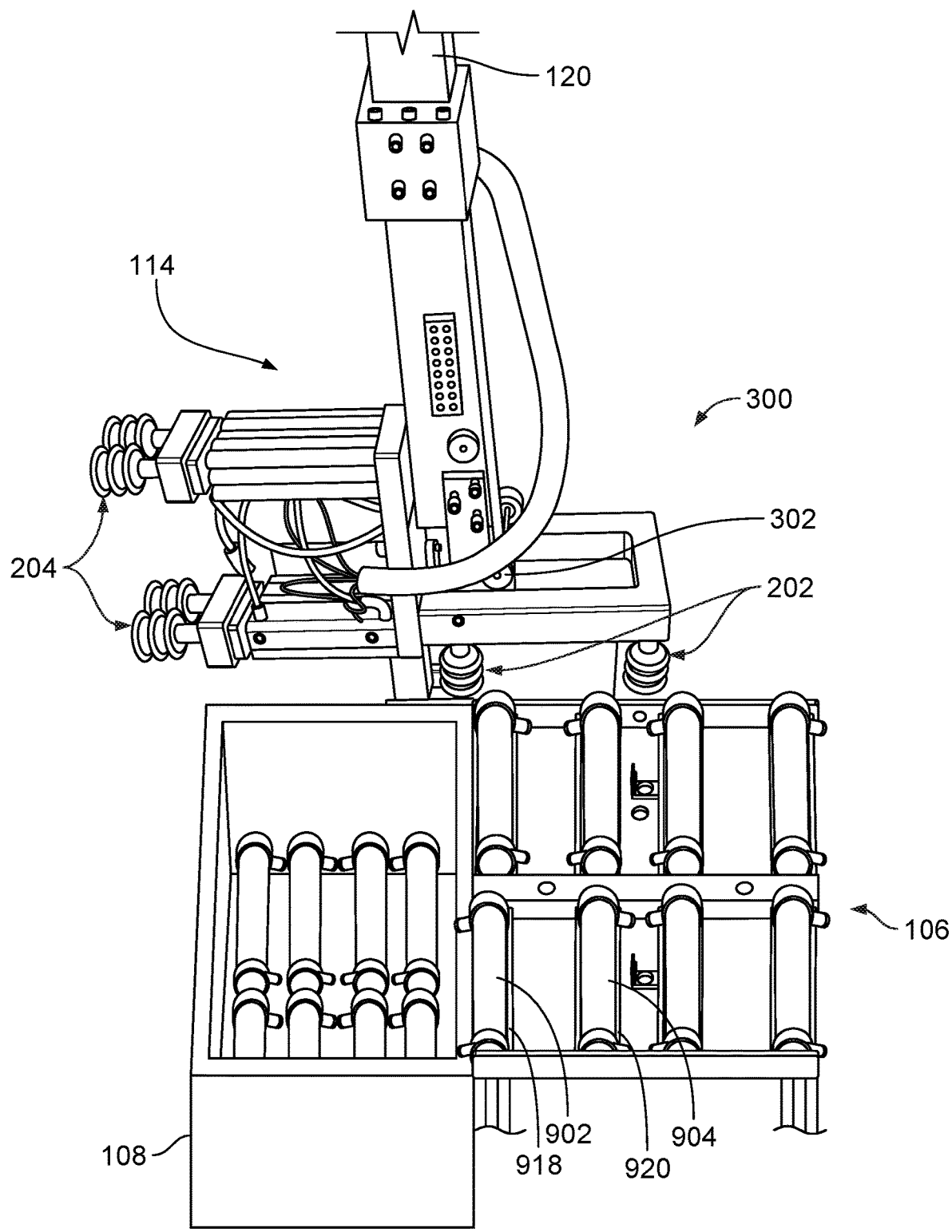
Figure 16:
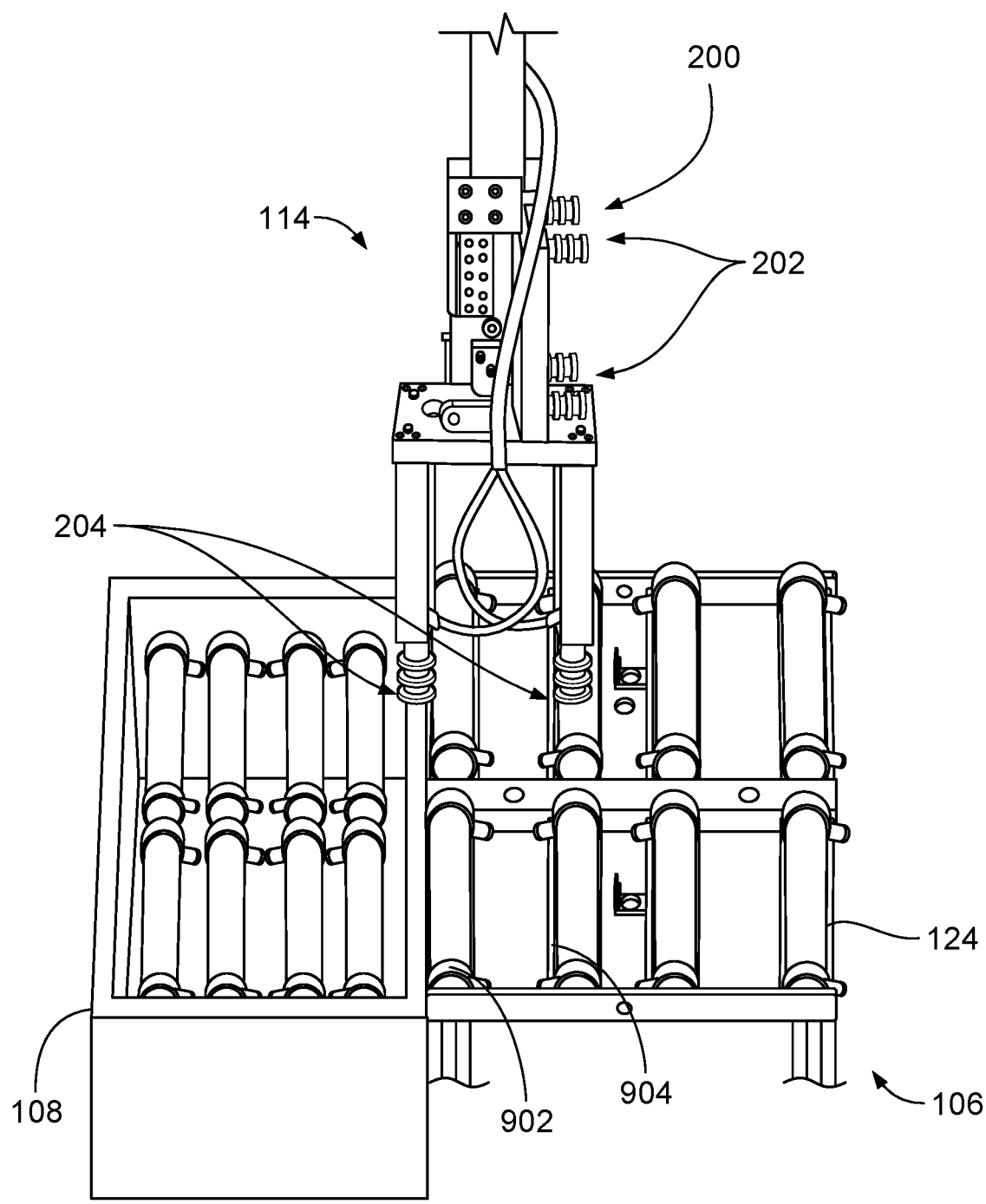

Referring to FIG. 15, once the dialyzer housings 902, 904 have been placed on the cooling racks 918, 920 and released from the arm tool 114, the vertical projection 120 of the robotic arm 104 retracts to lift the arm tool 114 above the cooling table 106. Once lifted above the cooling table 106 a predetermined distance, as measured by rotary encoders of the robotic arm 104, the controller 162 controls the arm tool 114 to rotate about the pin connector 302 from the second position 300 (as depicted in FIG. 15) to the first position 200 (as depicted in FIG. 16). As previously discussed, the arm tool 114 includes a pneumatic cylinder (not shown) that applies a force to an end of the arm tool 114 and causes the arm tool to rotate about the pin connector 302. The controller 160 coordinates the rotation of the arm tool 114 from the second fixed position 300 to the first fixed position 200 based on the spatial positioning of the arm tool 114. For example, the controller 162 is programmed to rotate the arm tool 114 from the second position 300 to the first position 200 at a specific point in the sequence of movements of the manufacturing cycle and based on the position of the arm tool 114 in three-dimensional space.

Figure 17:
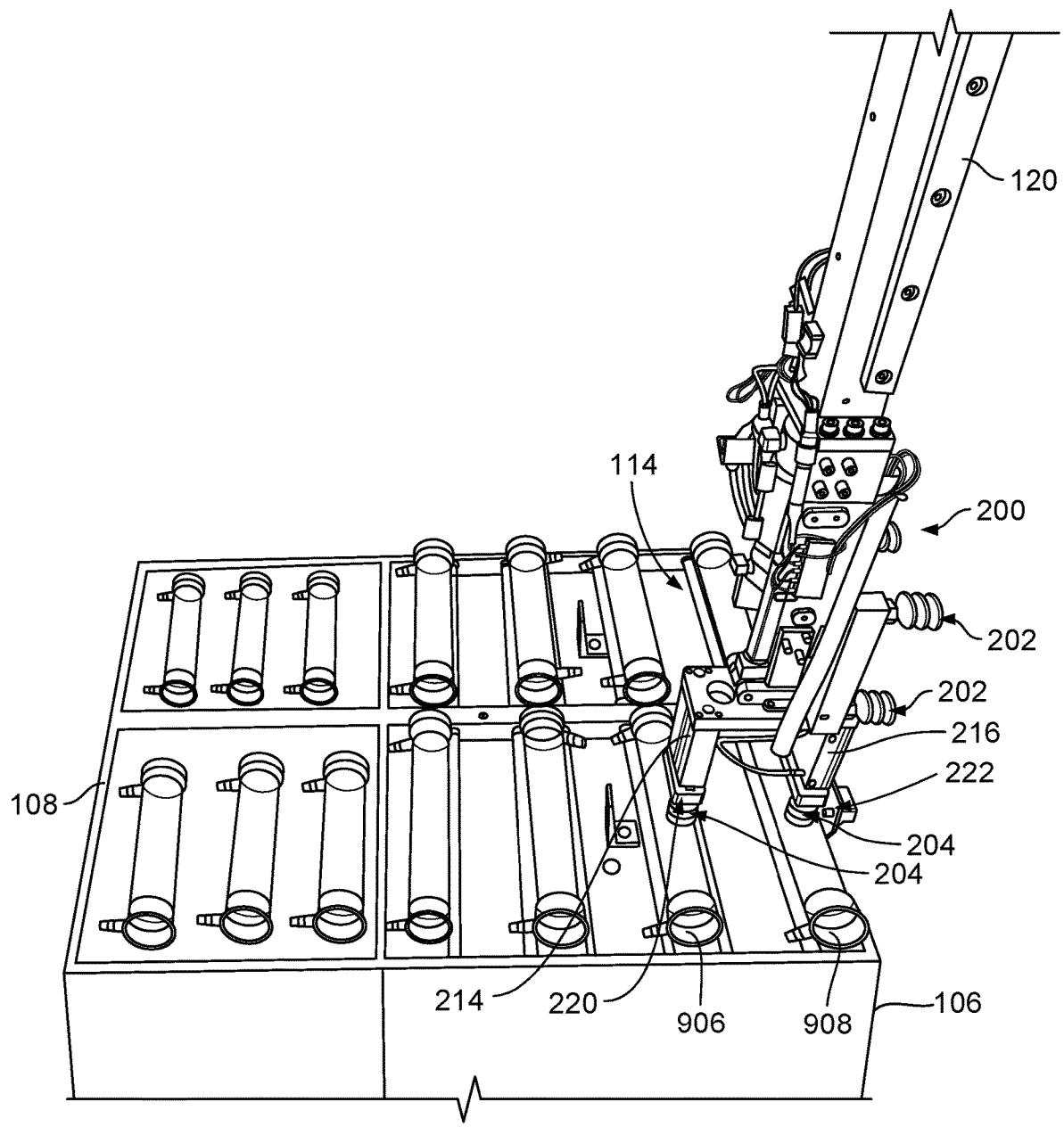

Referring to FIG. 17, once the arm tool 114 is in the first position with the second set of suction cups 204 facing downwards towards the cooling table 106, the vertical projection 120 of the robotic arm 104 translates along the lateral boom 118 until the controller 160 receives a signal with coordinates indicating that the second set of suction cups 204 is positioned over the center of a second pair of dialyzer housings 906, 908 on the cooling table 106. In addition, if necessary, the lateral boom 118 of the robotic arm 104 travels along the tracks 122 of the base 116 of the robotic arm 104 until the controller 160 receives a signal from the rotary encoder(s) that indicates that the robot has reached a position with corresponding with the second set of suction cups 204 being positioned over the center of the second pair of dialyzer housings 906, 908 on the cooling table 106. As depicted in FIG. 17, the first pair of suction cups 220 of the second set 202 is aligned with the first dialyzer housing 906, and the second pair of suction cups 222 of the second set 202 is aligned with the second dialyzer housing 908 to enable each pair of suction cups 220, 222 to couple with the respective dialyzer housing 906, 908.

Still referring to FIG. 17, once the pairs of suction cups 220, 222 of the second set 204 are positioned over the centers of the respective dialyzer housings 906, 908, the controller 162 controls the vertical projection 120 of the robotic arm 104 to extend a predetermined distance to lower the arm tool 114 towards the dialyzer housings 906, 908. In addition, the controller 162 controls vacuum suction to be applied through the vacuum lines 152, 154, 156 to the pairs of suction cups 220, 222, and through the center of each suction cup in the pairs of suction cups 220, 222 in order to couple the dialyzer housings 906, 908 to the pairs of suction cups 220, 222. The vertical projection 120 continues to extend until the controller 160 receives a signal from the rotary encoders indicating that the vertical projection 120 has extended a predetermined distance and receives a signal from a vacuum confirmation sensor indicating that the first and second pairs of suction cups 220, 222 are in contact with the surface of the dialyzer housings 906, 908 and coupled to the dialyzer housings 906, 908, respectively.

Figure 18:
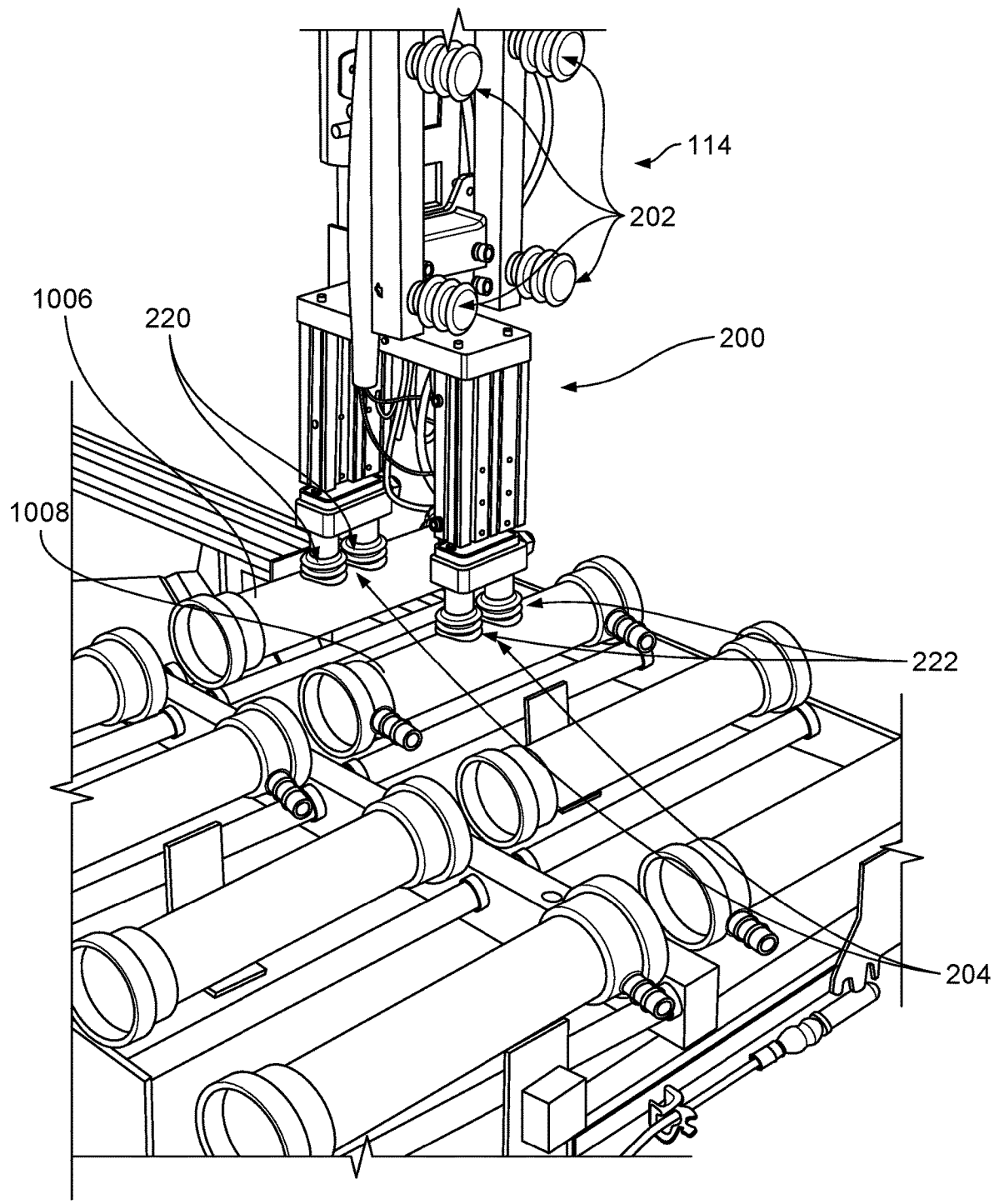

As previously discussed, each suction cup in the pairs 220, 222 includes an opening through its center, and each suction cup in the pairs 220, 222 is fluidly coupled to a vacuum source (e.g., vacuum source 150 of FIG. 1) via vacuum lines 152, 154, 156, enabling suction to be applied through the center of each suction cup. The suction force applied through the pairs of suction cups 220, 222 is transferred to the surface of the dialyzer housings 906, 908, which couples the dialyzer housings 906, 908 to the suction cup pairs 220, 222. FIG. 18 depicts a perspective view of the arm tool 114 positioned to couple a pair of dialyzer housings 1006, 1008 to the first and second pairs of suction cups 220, 222, respectively, of the second set of suction cups 204 in order to remove the dialyzer housings 1006, 1008 from the cooling table 106.

Figure 19:
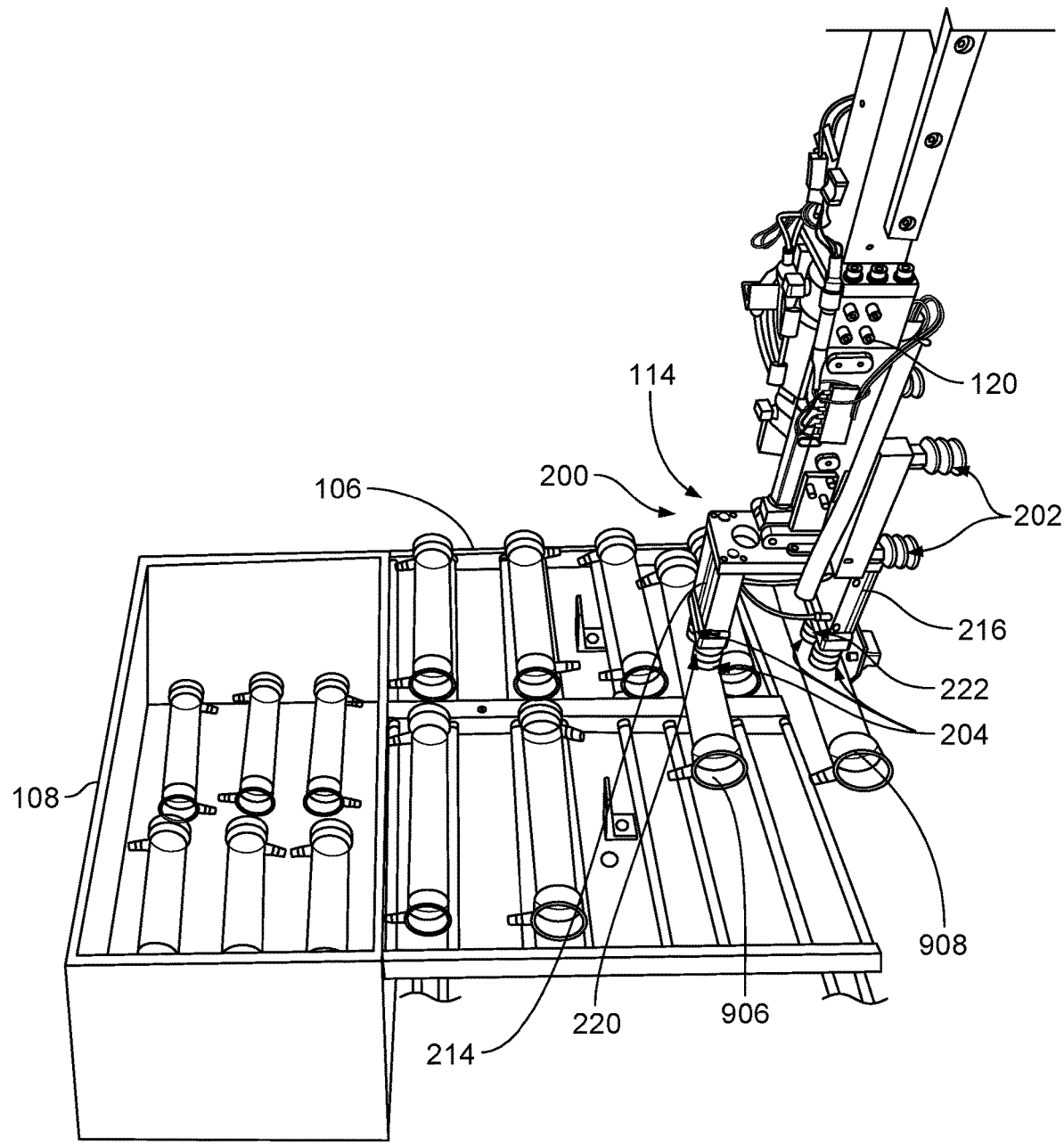

Referring to FIG. 19, once suction has been applied to the dialyzer housings 906, 908 to couple the dialyzer housings 906, 908 to the pairs of suction cups 220, 222, as determined based on a signal received by the controller 162 from a vacuum confirmation sensor (not shown), the controller 162 controls the vertical projection 120 of the robotic arm 104 to retract to lift the dialyzer housings 906, 908 off the cooling table 106. As the vertical projection 120 retracts, suction is continually applied through the pairs of suction cups 220, 222 to maintain the coupling of the dialyzer housings 906, 908 to the arm tool 114.

Figure 20:
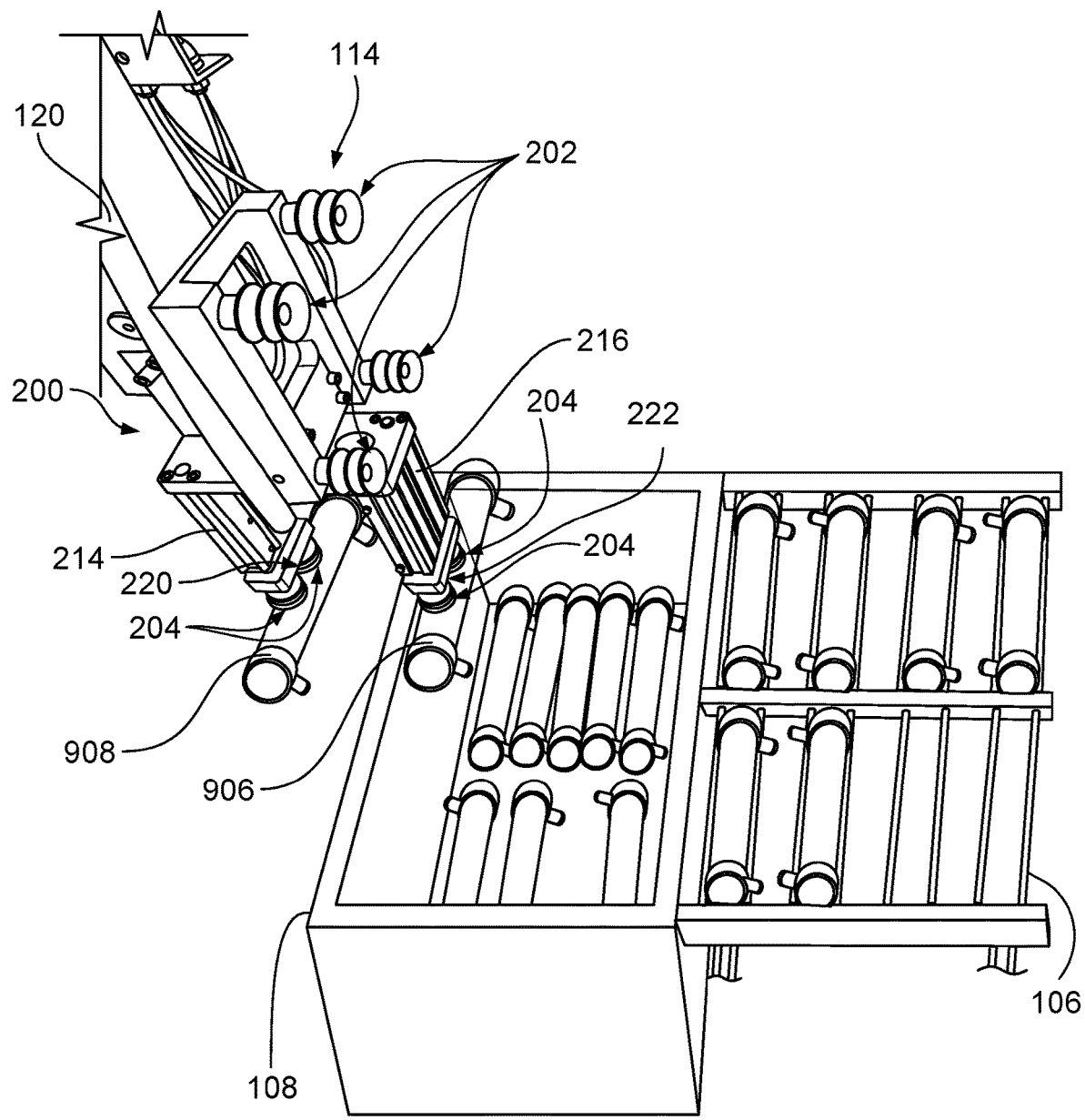

The vertical projection 120 travels along the lateral boom 118 of the robotic arm 104 until the controller 162 receives a signal from the rotary encoder(s) that the vertical projection 120 has travelled a predetermined distance corresponding with a position of the arm tool 114 in three-dimensional space that positions the second set of suction cups 204 over the storage container 108, as depicted in FIG. 20. In addition, if necessary, the lateral boom 118 of the robotic arm 104 travels along the tracks 122 of the base 116 of the robotic arm 104 until the controller 160 receives a signal from the rotary encoder(s) that the lateral boom 118 has travelled a predetermined distance corresponding with a position of the arm tool 114 in three-dimensional space that positions the second set of suction cups 204 over the storage container 108.

Figure 21:
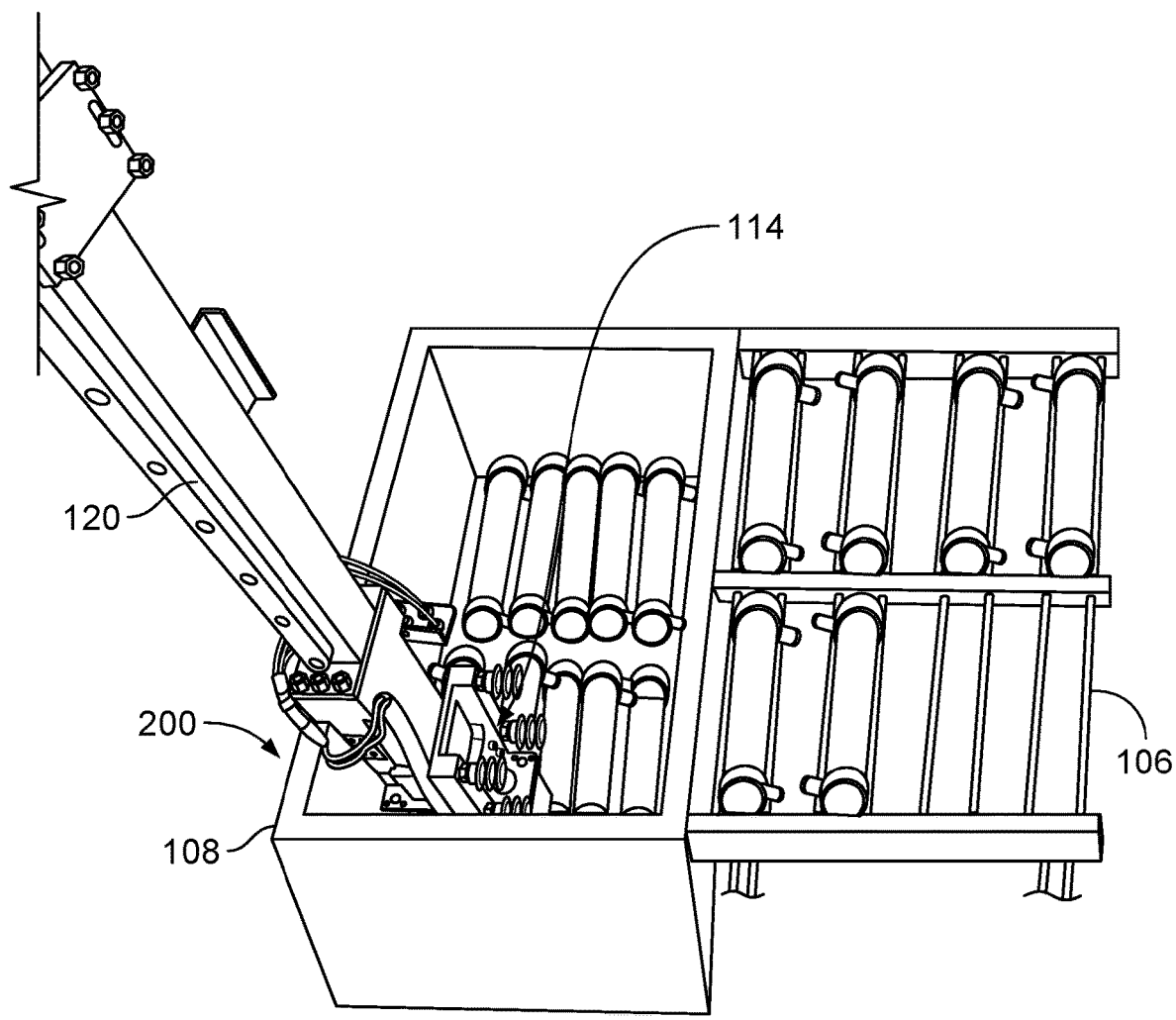

Referring to FIG. 21, once the arm tool 114 is positioned over the storage container 108, the vertical projection 120 of the robotic arm 104 extends a predetermined amount, as determined by the rotary encoders of the robotic arm 104, to lower the dialyzer housings 906, 908 into the storage container 108. The controller controls the movement of the robotic arm 104 components to position the housings 906 and 908 at has a programmed position in three-dimensional space. Once the housings 906, 908 are positioned in the predetermined position, as determined based on the position of the arm tool 114 determined based on signals transmitted by the rotary encoders of the robotic arm 104, the controller 162 stops the application of the vacuum suction through the second set of suction cups 204 to decouple the housings 906, 908 from the suction cups 204 and place the housings 906, 908 in the predetermined position in the container 108. As the container 108 fills with dialyzer housings, the controller 162 tallies the number of housings placed in the container to determine the unique position for placing each housing in the spatial volume of the container 108. By coupling the cooled dialyzer housings 906, 908 to the second set of suction cups 204 with the arm tool 114 in the first position 200, the length of the posts 214, 216 is maximized, which allows the dialyzer housings 906, 908 to be placed at the bottom of the storage container 108 without dropping the dialyzer housings 906, 908 a significant distance. As such, the risk of damage to the dialyzer housings 906, 908 during packing of the housings 906, 908 in the storage container 108 is reduced.

Before being moved into the storage container 108, the surface of the second pair of dialyzer housings 906, 908 is allowed to cool on the cooling table 106 to a temperature ranging between about 200° F. to about 250° F. In some examples, the dialyzer housings 906, 908 each rest on the cooling table 106 about 51 seconds to about 70 seconds before being packed in the storage container 108.

Once the dialyzer housings 906, 908 have been placed in the storage container 108 and released from the arm tool 114, the vertical projection 120 of the robotic arm 104 retracts to raise the arm tool 114 out of the storage container 108. In some implementations, after raising the arm tool 114 out of the storage container 108, the vertical projection 120 moves along the lateral boom 118 and the lateral boom 118 moves along the base 116 to reposition the robotic arm 104 and arm tool 114 over the injection molding device 102 in preparation for retrieving another set of dialyzer housings from the injection molding device 102. For example, after raising the arm tool 114 out of the storage container 108, the robotic arm moves to the position depicted in FIG. 6 in preparation for retrieving another pair of dialyzer housings from the injection molding device 102.

This dialyzer housing manufacturing process continues until the storage container 108 is filled with dialyzer housings. Once filled, the storage container 108 is replaced with a new, empty storage container, and the process continues. The filled storage container 108 can be used to pack or store the dialyzer housings within the storage container 108.

While certain embodiments have been described above, other embodiments are possible.

For example, while the method of demolding and packing the dialyzer housings has been described as relying signals received from rotary encoders to determine the coordinates of the arm tool 114 in three-dimensional space in order to coordinate the movements of the injection molding device 102, the movements of the robotic arm 104, the rotation of the arm tool 114, and the application of vacuum suction, alternatively, the movements of the injection molding device 102, the robotic arm 104, the rotation of the arm tool 114, and/or the application of vacuum suction through the suction cups 202, 204 can be coordinated based on timing. For example, the robotic arm 104 moves between each of the positions of the manufacturing cycle at a predictable rate. Therefore, the times at which rotation of the arm tool 114 between the first position 200 and the second position 300 should occur can be determined. Further, the times at which vacuum suction should be applied through each of the sets of suction cups 202, 204 to couple the dialyzer housings to the appropriate set of suction cups 202, 204 can be determined. Based on this determination, the controller 160 can be programmed to automatically move the robotic arm 104, rotate the arm tool 114, and apply vacuum suction through the suction cup sets 202, 204 at predetermined times throughout the manufacturing cycle.

While the system 100 has been described as including a robotic arm 104 with a lateral boom 118 and vertical projection 120, other types of robotic components may be used to position the arm tool 114 and perform the method of demolding and packing the dialyzer housings.

While the arm tool 114 has been described as including rectangular platform 206 and a U-shaped platform 212 with particular dimensions, platforms of other sizes and shapes can be used to support the suction cups of the arm tool 114. In addition, while the widths 270, 370 of the profile of the arm tool 114 in the first and second positions 200, 300 have been described as being about 16 cm to about 17 cm (e.g., about 16.5 cm) and about 35 cm to about 36 cm (e.g., about 35.5 cm), respectively, the arm tool 114 can be configured to have different profile widths in each position 200, 300.

While the arm tool 114 has been described as including 8 total suction cups, other numbers of suction cups are possible. For example, in some implementations, the arm tool includes four total suction cups, with two suction cups in the first set 202 and two suction cups in the second set 204. In this arrangement, one suction cup is coupled to each post 214, 216 of the U-shaped platform 212, and one suction cup is attached to each end of the rectangular platform 206. Further, in implementations in which the arm tool 114 includes a total of four suction cups, a single suction cup is used to couple the arm tool 114 to a single dialyzer housing. Alternatively, the arm tool can include a greater number of suction cups (e.g., 12 total suction cups, 16 total suction cups, etc.).

Further, while the arm tool 114 has been described as having an equal number of suction cups in the first set 202 and the second set 204, alternatively, the first set of suction cups 202 and the second set of suction cups 204 can each include a different number of suction cups.

In addition, while the arm tool 114 has been described as having a first set of suction cups 202 that is oriented about 90 degrees relative to the second set of suction cups 204, other orientations of the first and second set of suction cups can be used. For example, in some implementations, the first set of suction cups 202 is oriented about 70 degrees to about 110 degrees relative to the second set of suction cups 204. In some implementations, the first set of suction cups 202 is oriented about 70 degrees to about 110 degrees relative to the second set of suction cups 204.

While the arm tool 114 has been described as being configured to couple to two of dialyzer housings simultaneously, alternatively, the arm tool 114 can be configured to couple to other numbers of dialyzer housings. In some implementations, the arm tool 114 can be configured to couple to a single dialyzer housing. For example, the arm tool 114 can include a total of two suction cups: a first suction cup coupled to a first portion of the frame of the tool (e.g., the rectangular platform 206) and a second suction cup coupled to a second portion of the frame of the tool (e.g., the U-shaped platform 212), and the tool 114 can be configured to couple to a single dialyzer housing. Alternatively, the arm tool 114 can be configured to couple to three or more dialyzer housings simultaneously.

Similarly, while the injection molding device 102 has been described being configured to form two dialyzer housings simultaneously, alternatively, the injection molding device 102 may be configured to form a different number of dialyzer housings (e.g., 1, 3, 4, etc.).

While the robotic arm tool 114 has been described as rotating about 90 degrees between a first position 200 and a second position 300, the arm tool 114 can be controlled to rotate a different amount between the first position 200 and the second position 300. For example, in some implementations, the arm tool 114 rotates between about 70 degrees and about 110 degrees between the first position 200 and the second position 300.

In addition, while the arm tool 114 has been described as rotating between a first fixed position 200 and a second fixed position 300, alternatively, the arm tool 114 can move fluidly between various positions during the manufacturing cycle without stopping at fixed positions.

While the robotic arm 104 and arm tool 114 have been described as being used in a system for manufacturing dialyzer housings, alternatively, the robotic arm 104 and arm tool 114 can be used for manufacturing other items. For example, the robotic arm 104 and the arm tool 114 can be used to demold other types of components from an injection mold.

While the arm tool 114 has been described as being coupled to the robotic arm 104 with a pin connector 302, alternatively, other coupling mechanisms can be used to couple the arm tool 114 to the robotic arm 104.

While the injection molding device 102 has been described as having four mold alignment pins, alternatively, the injection molding device 102 may include a different number of mold alignment pins (e.g., 2, 3, 5, 6, etc.). Similarly, while the injection molding device 102 has been described as having four core alignment pins, alternatively, the injection molding device 102 may include a different number of core alignment pins (e.g., 2, 3, 5, 6, etc.).

In addition, while the molding process has been described as moving the second mold half 112 about 230 mm apart from the first mold half 110, the mold can open other distances. For example, in some implementations, the second mold half 112 is moved about 200 mm to about 240 mm apart from the first mold half 110 to accommodate the insertion of the arm tool 114 (positioned in the first position 200) between the mold halves 110, 112.

A number of embodiments have been described. Nevertheless, it will be understood that various modifications may be made without departing from the spirit and scope of the disclosure. Accordingly, other embodiments are within the scope of the following claims.

What is claimed is:

1. A method comprising:
opening a mold to expose a first dialyzer housing;
coupling the first dialyzer housing to a first portion of a tool;
moving the tool to remove the first dialyzer housing from the mold;
rotating the tool about 70 degrees to about 110 degrees to orient the first portion of the tool in a first direction;
placing the first dialyzer housing at a first location using the tool;
rotating the tool about 70 degrees to about 110 degrees to orient a second portion of the tool in the first direction;
coupling a second dialyzer housing at the first location to the second portion of the tool; and
placing the second dialyzer housing at a second location using the tool wherein:
rotating the tool about 70 degrees to about 110 degrees to orient the first portion of the tool in the first direction comprises rotating the tool into a second position; and
rotating the tool about 70 degrees to about 110 degrees to orient the second portion of the tool in the first direction comprises rotating the tool into a first position, wherein a width of the tool in the first position is smaller than a width of the tool in the second position.

2. The method of claim 1, wherein the mold is opened about 200 mm to about 240 mm.

3. The method of claim 1, wherein coupling the first dialyzer housing to a first portion of a tool comprises inserting the tool between a first half of the mold and a second half of the mold.

4. The method of claim 3, wherein inserting the tool between a first half of the mold and the second half of the mold comprises extending a robotic arm coupled to the tool between the first half of the mold and the second half of the mold.

5. The method of claim 1, wherein coupling the first dialyzer housing to the first portion of the tool comprises:
positioning one or more suction cups coupled to the first portion of the tool proximate the first dialyzer housing; and
applying vacuum suction through an opening in each of the one or more suction cups.

6. The method of claim 5, wherein placing the first dialyzer housing at a first location using the tool comprises:
positioning the first dialyzer housing proximate the first location using the tool; and
stopping the application of vacuum suction through the opening of each of the one or more suction cups.

7. The method of claim 1, wherein coupling a second dialyzer housing at the first location to the second portion of the tool comprises:
positioning one or more suction cups coupled to the second portion of the tool proximate the second dialyzer housing; and
applying vacuum suction through an opening in each of the one or more suction cups.

8. The method of claim 7, wherein placing the second dialyzer housing at a second location using the tool comprises:
positioning the second dialyzer housing proximate the second location using the tool; and
stopping the application of vacuum suction through the opening of each of the one or more suction cups.

9. The method of claim 1, further comprising:
coupling a third dialyzer housing to the first portion of the tool; and moving the tool to remove the third dialyzer housing from the mold, wherein the first dialyzer housing and the third dialyzer housing are removed from the mold simultaneously.

10. The method of claim 1, further comprising:
coupling a fourth dialyzer housing at the first location to the second portion of the tool; and
placing the fourth dialyzer housing at the second location using the tool, wherein the second dialyzer housing and the fourth dialyzer housing are placed at the second location simultaneously.

11. The method of claim 1, wherein the first location comprises a cooling table.

12. The method of claim 1, wherein the second location comprises a storage container.

13. The method of claim 1, wherein an alignment pin of a first half of the mold remains partially inserted into a second half of the mold when the mold is opened.

14. The method of claim 1, wherein coupling the first dialyzer housing to a first portion of a tool comprises:
moving an ejector pin of the mold to eject the first dialyzer housing from the mold,
wherein movement of the ejection pin is coordinated with an application of vacuum suction to the first dialyzer housing.

15. The method of claim 1, wherein the width of the tool in the first position is about 16 cm to about 17 cm.

16. The method of claim 1, wherein the width of the tool in the second position is about 35 cm to about 36 cm.

17. The method of claim 1, wherein placing the second dialyzer housing at the second location using the tool comprises:
determining, using a vacuum confirmation sensor of the tool, that the second dialyzer housing is coupled to the second portion of the tool; and
in response to determining that the second dialyzer housing is coupled to the second portion of the tool, moving the tool to place the second dialyzer housing at the second location.

18. The method of claim 1, wherein:
the first portion of the tool comprises a rectangular frame;
the second portion of the tool comprises a U-shaped platform comprising:
a first post;
a second post parallel with the first post; and
a connector bar, the first post, the second post and the first portion of the tool being coupled to the connector bar.

19. The method of claim 18, wherein:
the tool comprises:
four suction cups coupled to the rectangular frame, each suction cup being positioned at a respective corner of the rectangular frame; and
coupling the first dialyzer housing to the first portion of the tool comprises applying vacuum suction through an opening in each of the four suction cups.

20. The method of claim 19, wherein placing the first dialyzer housing at a first location using the tool comprises:
positioning the first dialyzer housing proximate the first location using the tool; and
stopping the application of vacuum suction through the opening in each of the four suction cups.

21. The method of claim 18, wherein:
the tool comprises:
a first pair of suction cups coupled to an end of the first post; and
a second pair of suction cups coupled to an end of the second post; and
coupling the second dialyzer housing at the first location to the second portion of the tool comprises applying vacuum suction through an opening in each suction cup of the first pair of suction cups and the second pair of suction cups.

22. The method of claim 21, wherein placing the second dialyzer
housing at the second location using the tool comprises:
positioning the second dialyzer housing proximate the second location using the tool; and
stopping the application of vacuum suction through an opening in each suction cup of the first pair of suction cups and the second pair of suction cups.

23. The method of claim 1, wherein:
a pin rotatably couples the tool to a robotic arm; and
rotating the tool comprises rotating the tool about the pin.

24. The method of claim 1, wherein rotating the tool comprises applying a force to the tool by a pneumatic cylinder.

* * * * *

UNITED STATES PATENT AND TRADEMARK OFFICE
CERTIFICATE OF CORRECTION

| | | |
|---|---|---|
| PATENT NO. | : 11,623,377 B2 | Page 1 of 1 |
| APPLICATION NO. | : 16/703287 | |
| DATED | : April 11, 2023 | |
| INVENTOR(S) | : Bryce Aaron Virgil and Bill Ray Cower | |

It is certified that error appears in the above-identified patent and that said Letters Patent is hereby corrected as shown below:

In the Claims

Column 18, Line 12, in Claim 1, after "tool" insert --;--.

Signed and Sealed this
Thirtieth Day of May, 2023

Katherine Kelly Vidal
*Director of the United States Patent and Trademark Office*